US012807926B2

(12) United States Patent
Gao et al.

(10) Patent No.: US 12,807,926 B2
(45) Date of Patent: Nov. 24, 2026

(54) GENETICALLY ENGINEERED ERYTHROCYTES CARRYING ANTI-PD-1 SINGLE CHAIN ANTIBODY AND PREPARATION METHOD THEREFOR

(71) Applicant: WESTLAKE THERAPEUTICS (HANGZHOU) CO. LIMITED, Hangzhou (CN)

(72) Inventors: Xiaofei Gao, Hangzhou (CN); Yanjie Huang, Hangzhou (CN); Dandan Li, Hangzhou (CN)

(73) Assignee: WESTLAKE THERAPEUTICS (HANGZHOU) CO. LIMITED, Hangzhou (CN)

( * ) Notice: Subject to any disclaimer, the term of this patent is extended or adjusted under 35 U.S.C. 154(b) by 1300 days.

(21) Appl. No.: 17/595,183

(22) PCT Filed: May 13, 2019

(86) PCT No.: PCT/CN2019/086602
§ 371 (c)(1),
(2) Date: Nov. 10, 2021

(87) PCT Pub. No.: WO2020/227885
PCT Pub. Date: Nov. 19, 2020

(65) Prior Publication Data

US 2024/0043802 A1 Feb. 8, 2024

(30) Foreign Application Priority Data

May 10, 2019 (CN) ........................ 201910387639.2

(51) Int. Cl.
*C12N 5/078* (2010.01)
*C07K 16/28* (2006.01)
*C12N 15/86* (2006.01)

(52) U.S. Cl.
CPC ........ *C12N 5/0641* (2013.01); *C07K 16/2818* (2013.01); *C12N 15/86* (2013.01); *C07K 2317/622* (2013.01); *C12N 2500/32* (2013.01); *C12N 2501/125* (2013.01); *C12N 2501/14* (2013.01); *C12N 2501/2303* (2013.01); *C12N 2501/2306* (2013.01); *C12N 2501/26* (2013.01); *C12N 2501/33* (2013.01); *C12N 2501/998* (2013.01); *C12N 2506/11* (2013.01); *C12N 2510/00* (2013.01); *C12N 2740/15043* (2013.01)

(58) Field of Classification Search
None
See application file for complete search history.

(56) References Cited

U.S. PATENT DOCUMENTS

2014/0255369 A1 9/2014 Turner et al.
2014/0273211 A1 9/2014 Slukvin et al.

FOREIGN PATENT DOCUMENTS

| | | | |
|---|---|---|---|
| CN | 101310007 | A | 11/2008 |
| CN | 103667188 | A | 3/2014 |
| CN | 107429230 | A | 12/2017 |
| CN | 107663515 | A | 2/2018 |
| CN | 108398361 | A | 8/2018 |
| CN | 109609533 | A | 4/2019 |
| CN | 109652369 | A | 4/2019 |
| WO | 1999/061584 | A1 | 12/1999 |
| WO | 2006/113881 | A2 | 10/2006 |
| WO | 2007038664 | A1 | 4/2007 |
| WO | 2013/023015 | A2 | 2/2013 |
| WO | 2016/123100 | A1 | 8/2016 |
| WO | WO 2020/173466 | A1 | 9/2020 |

OTHER PUBLICATIONS

Schippel et al. Experimental hematology 123 (2023): 1-17. (Year: 2023).*
Ando, et al., Experimental Hematology (2000) 28: 690-699 (Year: 2000).*
Boehm et al., Journal of Biotechnology (2009) 144: 127-134 (Year: 2009).*
Hamdy et al. Journal of immunological methods 297.1-2 (2005): 109-124 (Year: 2005).*
Logan et al. Current opinion in biotechnology 13.5 (2002): 429-436. (Year: 2002).*
Shariati et al. Journal of Isfahan Medical School 33.326 (2015): 305-315. (Year: 2015).*
Farazmandfar et al. Cell Journal (Yakhteh) 14.2 (2012): 76. (Year: 2012).*
Xu-Monnette et al. Blood, The Journal of the American Society of Hematology 131.1 (2018): 68-83 (Year: 2018).*
Rafiq et al. Nature biotechnology 36.9 (2018): 847-856. (Year: 2018).*
Ren et al., "A Versatile System for Rapid Multiplex Genome-Edited CAR T Cell Generation," *Oncotarget*, vol. 8, No. 10, pp. 17002-17011, (2017).

(Continued)

*Primary Examiner* — Maria Marvich
*Assistant Examiner* — Brendan Thomas Tinsley
(74) *Attorney, Agent, or Firm* — Hoxie & Associates LLC

(57) ABSTRACT

Provided are a method for preparing genetically engineered erythrocytes carrying an anti-PD-1 single chain antibody, and genetically engineered erythrocytes carrying the anti-PD-1 single chain antibody. The preparation method comprises the following steps: constructing a desired fragment sequence in a lentiviral expression vector, lentivirally packaging the vector of the desired sequence to obtain a high-titer lentiviral concentrate; isolating $Lin^{-}CD34^{-}$ cells from peripheral blood mononuclear cells and enriching the $Lin^{-}CD34^{-}$ cells; inducing the $Lin^{-}CD34^{-}$ cells to differentiate into erythroid and performing proliferation thereon; using the lentiviral concentrate to infect the $Lin^{-}CD34^{-}$ cells; and obtaining mature anti-PD-1 scFv erythrocytes via erythrocyte enucleation. The present genetically engineered erythrocytes carrying the anti-PD-1 single chain antibody can perform the targeted delivery of an anti-PD-1 single-chain antibody to tumor tissues.

6 Claims, 20 Drawing Sheets

Specification includes a Sequence Listing.

(56) References Cited

OTHER PUBLICATIONS

Albeniz et al., "Isolation of hentatopoietic stenl cells and the effect of C1)38 expression during the early erythroid progenitor cell development process" Oncology Letters (2012) 3: 55-60 (Year: 2012).
Ando, et al., "Extensive generation of human cord blood CD34 + stem cells from Lin-co34-cells in a long-term in vitro system" Experimental Hematology (2000) 28: 690-699 (Year: 2000).
Boehm et al., "The potential of human peripheral blood derived CD34+ cells for ex vivo red blood cell production" Journal of Biotechnology (2009) 144: 127-134 (Year: 2009).
Gallacher, L., et al. "Isolation and characterization of human CD34-Lin- and CD34+Lin-hematopoietic stem cells using cell surface markers AC133 and CD7," Hematopoiesis, vol. 95, No. 9, pp. 2813-2820, (2000).
Guo et al., "CD34 Hematopoietic Stem Cells: Current Concepts and Controversies" Stem Cells (2003) 21:15-20 (Year: 2003).
Han et al., "The effects of plasma gelsolin on hun1an erythroblast 111aturation for erythrocyte production" Stem Cell Research (2018) 64-75 (Year: 2018).
Hu, B., et al. "Immunization delivered by lentiviral vectors for cancer and infectious diseases," Immunol. Rev., vol. 239, No. 1, pp. 45-61, (2011).
Mckee, C., et al. "Advances and challenges in stem cell culture," Colloids and Surfaces B: Biointerfaces, vol. 159, pp. 62-77, (2017).
Ronzoni, B., et al. "Erythroid Differentiation and Maturation from Peripheral CD34+ Cells in Liquid Culture: Cellular and Molecular Characterization," Blood Cells Mol Dis, vol. 40, No. 2, pp. 148-155, (2008), Abstract Only.
Van Veen et al., "Tissue engineering red blood cells: a therapeutic" J Tissue Eng Regen Med (2015) 9: 760-770 (Year: 2015).
Written Opinion for International Application No. PCT/CN2020/076820, mailed by the International Bureau on May 28, 2020, 6 pages.
Bai Cixian et al, "Preliminary Study on Isolation and Culture Characteristics Ex Vivo of Lin-CD34 Hematopoietic Stem Cells," Chin J Hematol., vol. 24, No. 2, pp. 105-106, (2003).
Bai Cixian et al, "Preliminary Study on Isolation and Culture Characteristics Ex Vivo of Lin-CD34 Hematopoietic Stem Cells," Chin J Hematol., vol. 24, No. 2, pp. 105-106, (2003), English Language Translation.

* cited by examiner

Donor 1

Donor 2

SEQUENCE LISTING

```
<160> NUMBER OF SEQ ID NOS: 6

<210> SEQ ID NO 1
<211> LENGTH: 1239
<212> TYPE: DNA
<213> ORGANISM: Artificial Sequence
<220> FEATURE:
<223> OTHER INFORMATION: Synthetic construct

<400> SEQUENCE: 1

atgtatggaa aaataatctt tgtattacta ttgtcagaaa ttgtgagcat atcagcagag      60

cagaaactca tctcagaaga ggatctgggt ggaggcggtt cagacatcca gatgacccag     120

tctccatcct cactgtctgc atctgtggga gacagagtct ccatcacttg tcgggcgagt     180

cagggtatta gcagctggtt agcctggtat cagcagaaac cagagaaagc ccctaagtcc     240

ctgatctatg ctgcatccaa tttacgaagt ggggtcccat caaggttcag cggcagtgga     300

tctgggacag atttcactct caccatcagc agcctgcagc ctgaagattt tgcaacttat     360

tactgccaac agtattatag ttaccctagg acgttcggcc aagggaccaa ggtggaaatc     420

aaaggtggag gcggttcagg cggaggtggc tctggcggtg gcggatcgca gctgcagctg     480

caggagtcgg gcccaggact ggtgaagcct tcggagaccc tgtccctcac ctgcactgtc     540

tctggtggct ccctcagcag gagtagtttc ttctggggct ggatccgtca gcccccaggg     600

aagggactgg agtggattgg gagtatctat tatagtggga gcacctacta caacccgtcc     660

ctcaagagtc gagtcaccat atccgtagac acgtccaaga accagttctc cctgaagctg     720

agctctgtga ccgccgcaga cacggctgtg tattactgtg tgagagatta cgatattttg     780

actggcgacg aggactactg gggccaggga accctggtca ccgtgtcctc aggcggtggc     840

ggatcgttaa gtaccactga ggtggcaatg cacacttcaa cttcttcttc agtcacaaag     900

agttacatct catcacagac aaatgatacg cacaaacggg acacatatgc agccactcct     960

agagctcatg aagtttcaga aatttctgtt agaactgttt accctccaga agaggaaacc    1020

ggagaaaggg tacaacttgc ccatcatttc tctgaaccag agataacact cattattttt    1080

ggggtgatgg ctggtgttat tggaacgatc ctcttaattt cttacggtat tcgccgactg    1140

ataaagaaaa gcccatctga tgtaaaacct ctcccctcac ctgacacaga cgtgccttta    1200
```

agttctgttg aaatagaaaa tccagagaca agtgatcaa 1239

<210> SEQ ID NO 2
<211> LENGTH: 1215
<212> TYPE: DNA
<213> ORGANISM: Artificial Sequence
<220> FEATURE:
<223> OTHER INFORMATION: Synthetic construct

<400> SEQUENCE: 2
atgtatggaa aaataatctt tgtattacta ttgtcagaaa ttgtgagcat atcagcagag 60
cagaaactca tctcagaaga ggatctgggt ggaggcggtt cagaaattgt gttgacacag 120
tctccagcca ccctgtcttt gtctccaggg gaaagagcca ccctctcctg cagggccagt 180
cagagtgtta gtagttactt agcctggtac caacagaaac ctggccaggc tcccaggctc 240
ctcatctatg atgcatccaa cagggccact ggcatcccag ccaggttcag tggcagtggg 300
tctgggacag acttcactct caccatcagc agcctagagc ctgaagattt tgcagtttat 360
tactgtcagc agagtagcaa ctggcctcgg acgttcggcc aagggaccaa ggtggaaatc 420
aaaggtggag gcggttcagg cggaggtggc tctggcggtg gcggatcgca ggtgcagctg 480
gtggagtctg gggggaggcgt ggtccagcct gggaggtccc tgagactcga ctgtaaagcg 540
tctggaatca ccttcagtaa ctctggcatg cactgggtcc gccaggctcc aggcaagggg 600
ctggagtggg tggcagttat ttggtatgat ggaagtaaaa gatactatgc agactccgtg 660
aagggccgat tcaccatctc cagagacaat tccaagaaca cgctgtttct gcaaatgaac 720
agcctgagag ccgaggacac ggctgtgtat tactgtgcga caaacgacga ctactggggc 780
cagggaaccc tggtcaccgt ctcctcaggc ggtggcggat cgttaagtac cactgaggtg 840
gcaatgcaca cttcaacttc ttcttcagtc acaaagagtt acatctcatc acagacaaat 900
gatacgcaca aacgggacac atatgcagcc actcctagag ctcatgaagt ttcagaaatt 960
tctgttagaa ctgtttaccc tccagaagag gaaaccggag aaagggtaca acttgcccat 1020
catttctctg aaccagagat aacactcatt atttttgggg tgatggctgg tgttattgga 1080
acgatcctct taatttctta cggtattcgc cgactgataa agaaaagccc atctgatgta 1140
aaacctctcc cctcacctga cacagacgtg cctttaagtt ctgttgaaat agaaaatcca 1200
gagacaagtg atcaa 1215

<210> SEQ ID NO 3
<211> LENGTH: 1275
<212> TYPE: DNA
<213> ORGANISM: Artificial Sequence
<220> FEATURE:
<223> OTHER INFORMATION: Synthetic construct

<400> SEQUENCE: 3
atgtatggaa aaataatctt tgtattacta ttgtcagaaa ttgtgagcat atcagcagag 60
cagaaactca tctcagaaga ggatctgggt ggaggcggtt caggcggagg tggctctggc 120
ggtggcggat cggaaattgt gttgacacag tctccagcca ccctgtcttt gtctccaggg 180
gaaagagcca ccctctcctg cagggccagt cagagtgtta gcagctactt agcctggtac 240
caacagaaac ctggccaggc tcccaggctc atcatctatg atgcatccaa cagggccact 300
ggcatcccag ccaggttcag tggcagtggg tctgggacag acttcactct caccatcagc 360
agcctagagc ctgaagattt tgcagtttat tactgtcagc agcgtagcaa ctggcctctc 420

```
actttcggcg gagggaccaa ggtggagatc aaaggtggag gcggttcagg cggaggtggc    480

tctggcggtg gcggatcgca ggtgcagctg gtggaatctg ggggagacgt ggtccagcct    540

gggaggtccc tgagactctc ctgtgcagcg tctggattaa ccttcactaa ctatggcttc    600

cactgggtcc gccaggctcc aggcaagggg ctggagtggg tggctgttat atggtatgat    660

ggaagtaaga aatattatgc agactccgtg aagggccgat tcaccatctc cagagacatt    720

tccaagaaca cgctgtatct gcaaatgaac aacctgagag ccgaggacac ggctgtgtat    780

tactgtgcga ctggggatga ctactggggc cagggaaccc tggtcaccgt ctcctcaggt    840

ggaggcggtt caggcggagg tggctctggc ggtggcggat cgttaagtac cactgaggtg    900

gcaatgcaca cttcaacttc ttcttcagtc acaaagagtt acatctcatc acagacaaat    960

gatacgcaca aacgggacac atatgcagcc actcctagag ctcatgaagt ttcagaaatt   1020

tctgttagaa ctgtttaccc tccagaagag gaaaccggag aaagggtaca acttgcccat   1080

catttctctg aaccagagat aacactcatt atttttgggg tgatggctgg tgttattgga   1140

acgatcctct taatttctta cggtattcgc cgactgataa agaaaagccc atctgatgta   1200

aaacctctcc cctcacctga cacagacgtg cctttaagtt ctgttgaaat agaaaatcca   1260

gagacaagtg atcaa                                                    1275
```

```
<210> SEQ ID NO 4
<211> LENGTH: 1983
<212> TYPE: DNA
<213> ORGANISM: Artificial Sequence
<220> FEATURE:
<223> OTHER INFORMATION: Synthetic construct

<400> SEQUENCE: 4

atgtatggaa aaataatctt tgtattacta ttgtcagaaa ttgtgagcat atcagcagag     60

cagaaactca tctcagaaga ggatctgggt ggaggcggtt cagacatcca gatgacccag    120

tctccatcct cactgtctgc atctgtggga gacagagtct ccatcacttg tcgggcgagt    180

cagggtatta gcagctggtt agcctggtat cagcagaaac cagagaaagc ccctaagtcc    240

ctgatctatg ctgcatccaa tttacgaagt ggggtcccat caaggttcag cggcagtgga    300

tctgggacag atttcactct caccatcagc agcctgcagc ctgaagattt tgcaacttat    360

tactgccaac agtattatag ttaccctagg acgttcggcc aagggaccaa ggtggaaatc    420

aaaggtggag gcggttcagg cggaggtggc tctggcggtg gcggatcgca gctgcagctg    480

caggagtcgg gcccaggact ggtgaagcct tcggagaccc tgtccctcac ctgcactgtc    540

tctggtggct ccctcagcag gagtagtttc ttctggggct ggatccgtca gcccccaggg    600

aagggactgg agtggattgg gagtatctat tatagtggga gcacctacta caacccgtcc    660

ctcaagagtc gagtcaccat atccgtagac acgtccaaga accagttctc cctgaagctg    720

agctctgtga ccgccgcaga cacggctgtg tattactgtg tgagagatta cgatattttg    780

actggcgacg aggactactg gggccaggga accctggtca ccgtgtcctc aggcggtggc    840

ggatcggaca tccagatgac ccagtctcca tcctcactgt ctgcatctgt gggagacaga    900

gtctccatca cttgtcgggc gagtcagggt attagcagct ggttagcctg gtatcagcag    960

aaaccagaga aagcccctaa gtccctgatc tatgctgcat ccaatttacg aagtggggtc   1020

ccatcaaggt tcagcggcag tggatctggg acagatttca ctctcaccat cagcagcctg   1080

cagcctgaag attttgcaac ttattactgc caacagtatt atagttaccc taggacgttc   1140

ggccaaggga ccaaggtgga aatcaaaggt ggaggcggtt caggcggagg tggctctggc   1200
```

-continued

```
ggtggcggat cgcagctgca gctgcaggag tcgggcccag gactggtgaa gccttcggag   1260

accctgtccc tcacctgcac tgtctctggt ggctccctca gcaggagtag tttcttctgg   1320

ggctggatcc gtcagccccc agggaaggga ctggagtgga ttgggagtat ctattatagt   1380

gggagcacct actacaaccc gtccctcaag agtcgagtca ccatatccgt agacacgtcc   1440

aagaaccagt tctccctgaa gctgagctct gtgaccgccg cagacacggc tgtgtattac   1500

tgtgtgagag attacgatat tttgactggc gacgaggact actggggcca gggaaccctg   1560

gtcaccgtgt cctcaggcgg tggcggatcg ttaagtacca ctgaggtggc aatgcacact   1620

tcaacttctt cttcagtcac aaagagttac atctcatcac agacaaatga tacgcacaaa   1680

cgggacacat atgcagccac tcctagagct catgaagttt cagaaatttc tgttagaact   1740

gtttaccctc cagaagagga aaccggagaa agggtacaac ttgcccatca tttctctgaa   1800

ccagagataa cactcattat ttttggggtg atggctggtg ttattggaac gatcctctta   1860

atttcttacg gtattcgccg actgataaag aaaagcccat ctgatgtaaa acctctcccc   1920

tcacctgaca cagacgtgcc tttaagttct gttgaaatag aaaatccaga gacaagtgat   1980

caa                                                                 1983
```

```
<210> SEQ ID NO 5
<211> LENGTH: 1960
<212> TYPE: DNA
<213> ORGANISM: Artificial Sequence
<220> FEATURE:
<223> OTHER INFORMATION: Synthetic construct

<400> SEQUENCE: 5
```

```
atgtatggaa aaataatctt tgtattacta ttgtcagaaa ttgtgagcat atcagcagag     60

cagaaactca tctcagaaga ggatctgggt ggaggcggtt cagacatcca gatgacccag    120

tctccatcct cactgtctgc atctgtggga gacagagtct ccatcacttg tcgggcgagt    180

cagggtatta gcagctggtt agcctggtat cagcagaaac cagagaaagc ccctaagtcc    240

ctgatctatg ctgcatccaa tttacgaagt ggggtcccat caaggttcag cggcagtgga    300

tctgggacag atttcactct caccatcagc agcctgcagc ctgaagattt tgcaacttat    360

tactgccaac agtattatag ttaccctagg acgttcggcc aagggaccaa ggtggaaatc    420

aaaggtggag gcggttcagg cggaggtggc tctggcggtg gcggatcgca gctgcagctg    480

caggagtcgg gcccaggact ggtgaagcct tcggagaccc tgtccctcac ctgcactgtc    540

tctggtggct ccctcagcag gagtagtttc ttctggggct ggatccgtca gcccccaggg    600

aagggactgg agtggattgg gagtatctat tatagtggga gcacctacta caacccgtcc    660

ctcaagagtc gagtcaccat atccgtagac acgtccaaga accagttctc cctgaagctg    720

agctctgtga ccgccgcaga cacggctgtg tattactgtg tgagagatta cgatattttg    780

actggcgacg aggactactg gggccaggga accctggtca ccgtgtcctc aggcggtggc    840

ggatcggaaa ttgtgttgac acagtctcca gccaccctgt ctttgtctcc aggggaaaga    900

gccaccctct cctgcagggc cagtcagagt gttagtagtt acttagcctg gtaccaacag    960

aaacctggcc aggctcccag gctcctcatc tatgatgcat ccaacagggc cactggcatc   1020

ccagccaggt tcagtggcag tgggtctggg acagacttca ctctcaccat cagcagccta   1080

gagcctgaag attttgcagt ttattactgt cagcagagta gcaactggcc tcggacgttc   1140

ggccaaggga ccaaggtgga aatcaaaggt ggaggcggtt caggcggagg tggctctggc   1200
```

ggtggcggat cgcaggtgca gctggtggag tctgggggag gcgtggtcca gcctgggagg 1260
tccctgagac tcgactgtaa agcgtctgga atcaccttca gtaactctgg catgcactgg 1320
gtccgccagg ctccaggcaa ggggctggag tgggtggcag ttatttggta tgatggaagt 1380
aaaagatact atgcagactc cgtgaagggc cgattcacca tctccagaga caattccaag 1440
aacacgctgt ttctgcaaat gaacagcctg agagccgagg acacggctgt gtattactgt 1500
gcgacaaacg acgactactg gggccaggga accctggtca ccgtctcctc aggcggtggc 1560
ggatcgttaa gtaccactga ggtggcaatg cacacttcaa cttcttcttc agtcacaaag 1620
agttacatct catcacagac aaatgatacg cacaaacggg acacatatgc agccactcct 1680
agagctcatg aagtttcaga aatttctgtt agaactgttt accctccaga agaggaaacc 1740
ggagaaaggg tacaacttgc ccatcatttc tctgaaccag agataacact cattattttt 1800
ggggtgatgg ctggtgttat tggaacgatc ctcttaattt cttacggtat tcgccgactg 1860
ataaagaaaa gcccatctga tgtaaaacct ctcccctcac ctgacacaga cgtgccttta 1920
agttctgttg aaatagaaaa tccagagaca agtgatcaag 1960

<210> SEQ ID NO 6
<211> LENGTH: 2679
<212> TYPE: DNA
<213> ORGANISM: Artificial Sequence
<220> FEATURE:
<223> OTHER INFORMATION: Synthetic construct

<400> SEQUENCE: 6
atgtatggaa aaataatctt tgtattacta ttgtcagaaa ttgtgagcat atcagcagag 60
cagaaactca tctcagaaga ggatctgggt ggaggcggtt cagacatcca gatgacccag 120
tctccatcct cactgtctgc atctgtggga gacagagtct ccatcacttg tcgggcgagt 180
cagggtatta gcagctggtt agcctggtat cagcagaaac cagagaaagc ccctaagtcc 240
ctgatctatg ctgcatccaa tttacgaagt ggggtcccat caaggttcag cggcagtgga 300
tctgggacag atttcactct caccatcagc agcctgcagc ctgaagattt tgcaacttat 360
tactgccaac agtattatag ttaccctagg acgttcggcc aagggaccaa ggtggaaatc 420
aaaggtggag gcggttcagg cggaggtggc tctggcggtg gcggatcgca gctgcagctg 480
caggagtcgg gcccaggact ggtgaagcct tcggagaccc tgtccctcac ctgcactgtc 540
tctggtggct ccctcagcag gagtagtttc ttctggggct ggatccgtca gcccccaggg 600
aagggactgg agtggattgg gagtatctat tatagtggga gcacctacta caacccgtcc 660
ctcaagagtc gagtcaccat atccgtagac acgtccaaga accagttctc cctgaagctg 720
agctctgtga ccgccgcaga cacggctgtg tattactgtg tgagagatta cgatattttg 780
actggcgacg aggactactg gggccaggga accctggtca ccgtgtcctc aggcggtggc 840
ggatcggaaa ttgtgttgac acagtctcca gccaccctgt ctttgtctcc aggggaaaga 900
gccaccctct cctgcagggc cagtcagagt gttagtagtt acttagcctg gtaccaacag 960
aaacctggcc aggctcccag gctcctcatc tatgatgcat ccaacagggc cactggcatc 1020
ccagccaggt tcagtggcag tgggtctggg acagacttca ctctcaccat cagcagccta 1080
gagcctgaag attttgcagt ttattactgt cagcagagta gcaactggcc tcggacgttc 1140
ggccaaggga ccaaggtgga aatcaaaggt ggaggcggtt caggcggagg tggctctggc 1200
ggtggcggat cgcaggtgca gctggtggag tctgggggag gcgtggtcca gcctgggagg 1260
tccctgagac tcgactgtaa agcgtctgga atcaccttca gtaactctgg catgcactgg 1320

-continued

```
gtccgccagg ctccaggcaa ggggctggag tgggtggcag ttatttggta tgatggaagt   1380

aaaagatact atgcagactc cgtgaagggc cgattcacca tctccagaga caattccaag   1440

aacacgctgt ttctgcaaat gaacagcctg agagccgagg acacggctgt gtattactgt   1500

gcgacaaacg acgactactg gggccaggga accctggtca ccgtctcctc aggcggtggc   1560

ggatcggaaa ttgtgttgac acagtctcca gccaccctgt ctttgtctcc aggggaaaga   1620

gccaccctct cctgcagggc cagtcagagt gttagcagct acttagcctg gtaccaacag   1680

aaacctggcc aggctcccag gctcatcatc tatgatgcat ccaacagggc cactggcatc   1740

ccagccaggt tcagtggcag tgggtctggg acagacttca ctctcaccat cagcagccta   1800

gagcctgaag attttgcagt ttattactgt cagcagcgta gcaactggcc tctcactttc   1860

ggcggaggga ccaaggtgga gatcaaaggt ggaggcggtt caggcggagg tggctctggc   1920

ggtggcggat cgcaggtgca gctggtggaa tctgggggag acgtggtcca gcctgggagg   1980

tccctgagac tctcctgtgc agcgtctgga ttaaccttca ctaactatgg catgcactgg   2040

gtccgccagg ctccaggcaa ggggctggag tgggtggctg ttatatggta tgatggaagt   2100

aagaaatatt atgcagactc cgtgaagggc cgattcacca tctccagaga catttccaag   2160

aacacgctgt atctgcaaat gaacaacctg agagccgagg acacggctgt gtattactgt   2220

gcgactgggg atgactactg gggccaggga accctggtca ccgtctcctc aggcggtggc   2280

ggatcgttaa gtaccactga ggtggcaatg cacacttcaa cttcttcttc agtcacaaag   2340

agttacatct catcacagac aaatgatacg cacaaacggg acacatatgc agccactcct   2400

agagctcatg aagtttcaga aatttctgtt agaactgttt accctccaga agaggaaacc   2460

ggagaaaggg tacaacttgc ccatcatttc tctgaaccag agataacact cattattttt   2520

ggggtgatgg ctggtgttat tggaacgatc ctcttaattt cttacggtat tcgccgactg   2580

ataaagaaaa gcccatctga tgtaaaacct ctcccctcac ctgacacaga cgtgccttta   2640

agttctgttg aaatagaaaa tccagagaca agtgatcaa                          2679
```

GENETICALLY ENGINEERED ERYTHROCYTES CARRYING ANTI-PD-1 SINGLE CHAIN ANTIBODY AND PREPARATION METHOD THEREFOR

CROSS-REFERENCE TO RELATED APPLICATIONS

This application is a U.S. National Stage Application under 35 U.S.C. § 371 of International Application No. PCT/CN2019/086602, which was filed on May 13, 2019, which claims priority to and Chinese Patent Application Serial No. 201910387639.2, which was filed on May 10, 2019, the contents of each of which are hereby incorporated by reference in their entireties.

REFERENCE TO A SEQUENCE LISTING

This application contains a Sequence Listing as a separate part of the disclosure. The Sequence Listing is incorporated herein by reference.

TECHNICAL FIELD

The present invention belongs to the field of medical biology, and particularly relates to genetically engineered erythrocytes carrying an anti-PD-1 single chain antibody and a preparation method therefor.

BACKGROUND

Immunotherapy has become one of very forceful means to treat cancer. There are more and more approved immunotherapeutic medicaments, as well as the projects in clinical and preclinical development. However, immunotherapy is a kind of extensive therapeutic strategy directed to the systemic immune system. Therefore, the key point still lies in the regulation of immune system. The current immunotherapy mainly has the following problems, such as, autoimmunity, nonspecific inflammation and other side effects. The key point is how to improve the therapeutic effect and control the adverse response via increasing the response rate of immunotherapy. How to perform in vivo delivery of medicaments (such as, anti-PD-1, CTLA-4 monoclonal antibodies, IL-2, TNF-α, and the like) for immunotherapy and to decrease toxic and side effects are to be explored and solved urgently.

With lots of unique characteristics, erythrocytes become a very attractive research object for the in vivo delivery of natural and synthetic components. 1) Erythrocytes have a wide circulation range, are numerous and can be used for carrying medicaments; 2) aged or damaged erythrocytes can be removed by a reticuloendothelial system, which can achieve complete biodegradation without any toxic substances; 3) erythrocytes, especially autologous erythrocyte, have good biocompatibility; 4) compared with other synthetic carriers, erythrocytes have longer circulating half-time (approximately 120 days for humans); 5) erythrocytes have no cell nucleus, no mitochondria and any DNA; any form of genetic engineering modification to the precursor of erythrocytes will be eliminated after the erythrocyte enucleation, therefore, erythrocytes will not cause abnormal growth or tumor formation after being imported into a recipient; 6) erythrocytes protect encapsulated substances from early inactivation and degradation, and protect an organism from the toxic effect of a medicament, and meanwhile also can be a bioreactor for protein medicaments.

Programmed cell death protein 1, also called PD-1 and CD279, is a protein on cell surface, and binds to its ligand PD-L1 to downregulate the response of immune system to human cells. It regulates the immune system and promotes self-tolerance by inhibiting the inflammatory activity of T cells. This can prevent autoimmune diseases, but it can also prevent the immune system from killing cancer cells. PD-1 is an immune checkpoint to prevent autoimmunity via two mechanisms. Firstly, PD-1 accelerates the apoptosis (programmed cell death) of antigen-specific T cells in the lymph nodes. Secondly, PD-1 decreases the apoptosis of regulatory T cells (anti-inflammatory, suppressor T cells). In neoplastic disease state, PD-L1 on tumor cells and PD-1 on T cells interact with each other to reduce the function signal of T cells, thus preventing the immune system to attack tumor cells. The use of an inhibitor (monoclonal antibody) for blocking the interaction of PD-L1 and PD-1 receptors can prevent cancer from escaping the immune system in such a way, thus achieving cancer therapy. The use of an anti-PD-1 monoclonal antibody can achieve significant therapeutic effects clinically directed to cancers including melanoma, head-neck carcinoma, renal cell carcinoma, non-small cell lung cancer, bladder cancer, colorectal cancer and other cancers. However, in these indications, only about 20-30% of terminal cancer patients respond to the anti-PD-1 monoclonal antibody therapy, and most of patients are not sensitive to the anti-PD-1 therapy. The main reason is that the medicament may not be targetedly delivered to a tumor tissue, is autoimmunogenic, and has lower utilization rate, meanwhile may cause higher systemic side effects from tumor immune medicaments.

SUMMARY

Directed against the shortcomings existing in the prior art, the present invention provides genetically engineered erythrocytes carrying an anti-PD-1 single chain antibody. The purpose is to solve the technical problems that the delivery of anti-PD-1 monoclonal antibodies cannot be targeted to tumor tissues, the utilization efficiency is lower, and higher systemic side effects from tumor immune medicaments are caused. The present invention further provides a method for preparing genetically engineered erythrocytes carrying an anti-PD-1 single chain antibody.

Specific technical solutions are as follows:

a method for preparing genetically engineered erythrocytes carrying an anti-PD-1 single chain antibody, comprising the following steps:

step S1: constructing a desired fragment sequence in a lentiviral expression vector to obtain a vector of the desired sequence, wherein the desired fragment is Anti-PD-1 scFv, and the Anti-PD-1 scFv represents an anti-PD-1 single-chain variable region fragment;

step S2: lentivirally packaging the vector of the desired sequence in the step S1 and obtaining a high-titer lentiviral concentrate after centrifuging and concentrating;

step S3: isolating $Lin^-CD34^-$ cells from peripheral blood mononuclear cells and enriching the $Lin^-CD34^-$ cells;

step S4: changing the culture medium of the $Lin^-CD34^-$ cells to a differentiation stage-1 culture medium, inducing the $Lin^-CD34^-$ cells to differentiate into erythroid, and performing proliferation thereon;

step S5: using the lentiviral concentrate in the step S2 to infect the $Lin^-CD34^-$ cells in the step S4 to obtain anti-PD-1 scFv $Lin^-CD34^-$ cells;

step S6: changing the culture medium of the anti-PD-1 scFv $Lin^{-}CD34^{-}$ cells to a differentiation stage-2 culture medium; wherein the anti-PD-1 scFv $Lin^{-}CD34^{-}$ cells are subjected to erythrocyte enucleation to obtain mature anti-PD-1 scFv erythrocytes, i.e., the genetically engineered erythrocytes carrying an anti-PD-1 single chain antibody.

In some embodiments, in the step S1, the Anti-PD-1 scFv has a nucleotide sequence shown as SEQ ID NO.1, SEQ ID NO.2, SEQ ID NO.3, SEQ ID NO.4, SEQ ID NO.5 and/or SEQ ID NO.6; the lentiviral expression vector is pCDH-MCS-T2A-copGFP-MSCV.

In some embodiments, in the step S2, the lentiviral package uses a three-plasmid packaging system; wherein the three-plasmid packaging system comprises a vector of the desired sequence, a PSPAX2 plasmid, and a VSVG plasmid; and the vector of the desired sequence, the PSPAX2 plasmid, and the VSVG plasmid have a ratio of 2:1:1; the lentiviral package uses HEK 293T cells as lentiviral packaging cells.

The centrifuging and concentrating has a rotary speed of 70000RCF, time of 2 h and a temperature of 4° C.

In some embodiments, in the step S3, cell resuspension is performed by a cell separation buffer solution added with bovine serum albumin and EDTA; a biotin-labeled antibody and a streptavidin-labeled magnetic bead are added to remove cells with a special surface marker, thus the $Lin^{-}CD34^{-}$ cells are isolated.

In some embodiments, in the step S3, a cytokine composition for the enrichment of the $Lin^{-}CD34^{-}$ cells comprises 50-100 ng/ml recombinant human fms-like tyrosine kinase 3 ligand, 50-100 ng/ml recombinant human stem cell factor, 50-100 ng/ml recombinant human interleukin 3, and 200-800 μg/ml recombinant human interleukin 6.

In some embodiments, in the step S4, the differentiation stage-1 culture medium comprises IMDM, 10-15% fetal calf serum, 5-10% human plasma, 1-4 mM glutamine, 1-2% bovine serum albumin, 300-600 μg/ml human transferrin, 8-13 μg/ml recombinant human insulin, 2% penicillin-streptomycin, 3-5 ng/ml recombinant human interleukin 3, 4-7 U/ml recombinant human erythropoietin and 100 ng/ml recombinant human stem cell factor.

In some embodiments, in the step S5, the infection step is as follows: resuspending the $Lin^{-}CD34^{-}$ cells in the differentiation stage-1 culture medium, calculating the infection volume and the virus dosage, and in terms of the infection volume, adding polybrene to the lentiviral concentrate in the amount of 10 μg/ml for mixed incubation for 5 min, then adding the incubated lentiviral concentrate to the cells and mixing thoroughly, wherein the lentiviral concentrate has a final concentration of $5\times10^{7}$ TU/ml-$5\times10^{8}$ TU/ml; using a horizontal rotor centrifugal machine for centrifugal infection with a rotary speed of 500×g, a temperature of 32° C. and a time of 90 min; after the centrifugation, placing the anti-PD-1 scFv $Lin^{-}CD34^{-}$ cells under conditions of 37° C. and 5% $CO_2$ for culture.

In some embodiments, in the step S6, the differentiation stage-2 culture medium comprises but not limited to IMDM, 15% fetal calf serum, 5-10% human plasma, 1-4 mM glutamine, 1-2% bovine serum albumin, 300-600 μg/ml human transferrin, 8-13 μg/ml recombinant human insulin, 2% penicillin-streptomycin, and 1-5 U/ml recombinant human erythropoietin.

The present invention further provides genetically engineered erythrocytes carrying an anti-PD-1 single chain antibody which is obtained according to the above preparation method.

The present invention has the following beneficial effects: erythrocyte has lots of unique characteristics specifically as follows: 1) erythrocytes have a wide circulation range, are numerous and can be used for carrying medicaments; 2) aged or damaged erythrocytes can be removed by a reticuloendothelial system, which can achieve complete biodegradation without any toxic substances; 3) erythrocytes, especially autologous erythrocyte, have good biocompatibility; 4) compared with other synthetic carriers, erythrocytes have longer circulating half-time (approximately 120 days for humans); 5) erythrocytes have no cell nucleus, no mitochondria and any DNA; any form of genetic engineering modification to the precursor of erythrocytes will be eliminated after the erythrocyte enucleation, therefore, erythrocytes will not cause abnormal growth or tumor formation after being imported into a recipient; 6) erythrocytes protect encapsulated substances from early inactivation and degradation, and protect an organism from the toxic effect of a medicament, and meanwhile also can be a bioreactor for protein medicaments. These features above make erythrocytes an important biological transport vehicle to deliver natural and synthetic components in vivo. In the method provided in the present invention for preparing the genetically engineered erythrocytes carrying an anti-PD-1 single chain antibody, erythrocytes were used as transport vehicles with the aid of the unique characteristics thereof, and were subjected to genetic engineering modification, such that erythrocyte membrane surface carried an antibody medicament (namely, anti-PD-1 single chain antibody) for tumor immunotherapy, afterwards, the genetically engineered precursor cells were induced to differentiate into mature erythrocytes by inducing erythroid differentiation means, thus the genetically engineered erythrocytes carrying the anti-PD-1 single chain antibody were obtained. The genetically engineered erythrocytes carrying an anti-PD-1 single chain antibody provided by the present invention perform targeted delivery of the anti-PD-1 single-chain antibody to tumor tissues, are more effective in exerting T cell activation function, and can significantly reduce the dosage of medicaments and alleviate the side effects of systemic tumor immune medicaments.

DETAILED DESCRIPTION OF THE EMBODIMENTS

Figure 1:
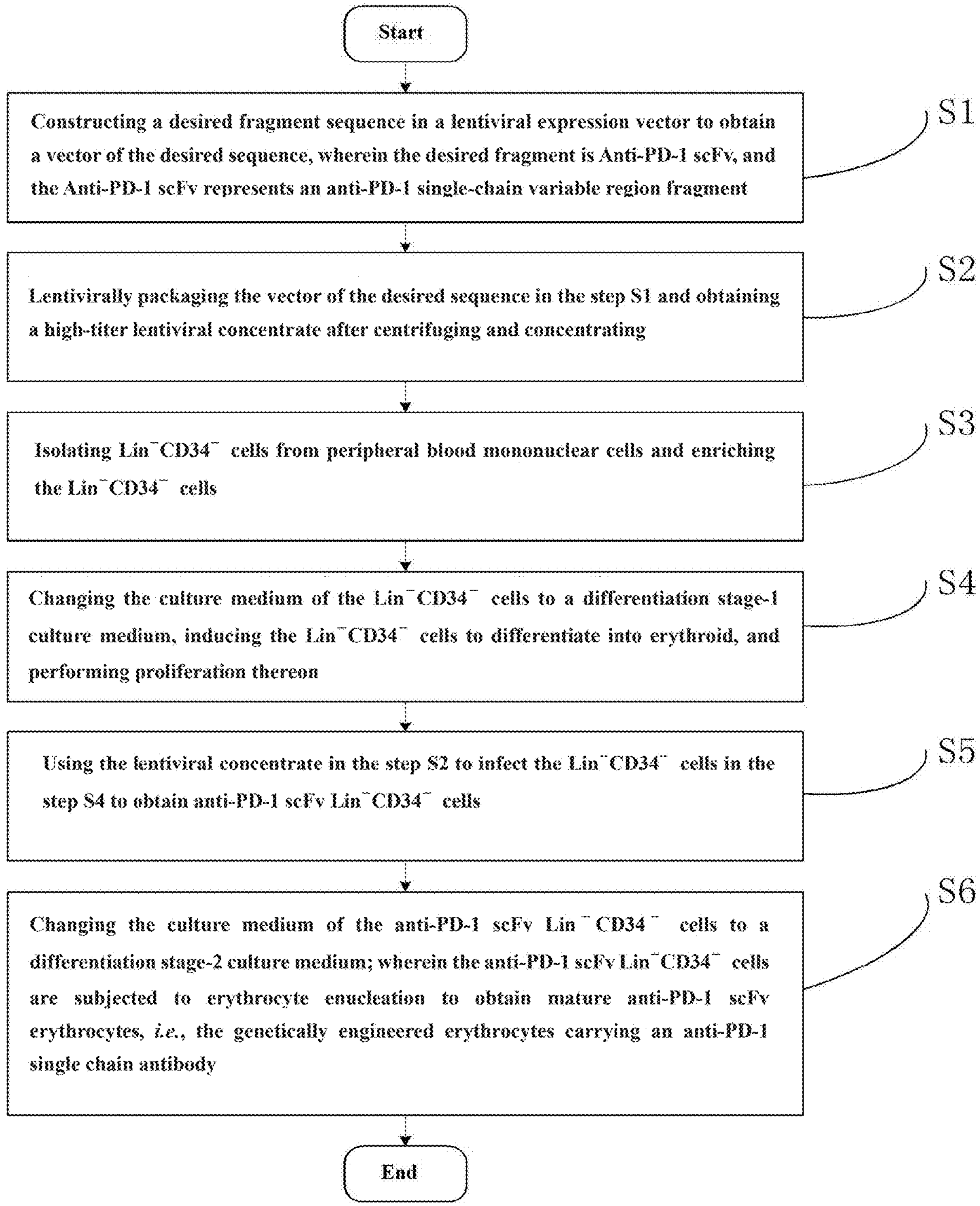
FIG. 1 is a flow diagram showing a method provided by the present invention for preparing genetically engineered erythrocytes carrying an anti-PD-1 single chain antibody.
Figure 2:
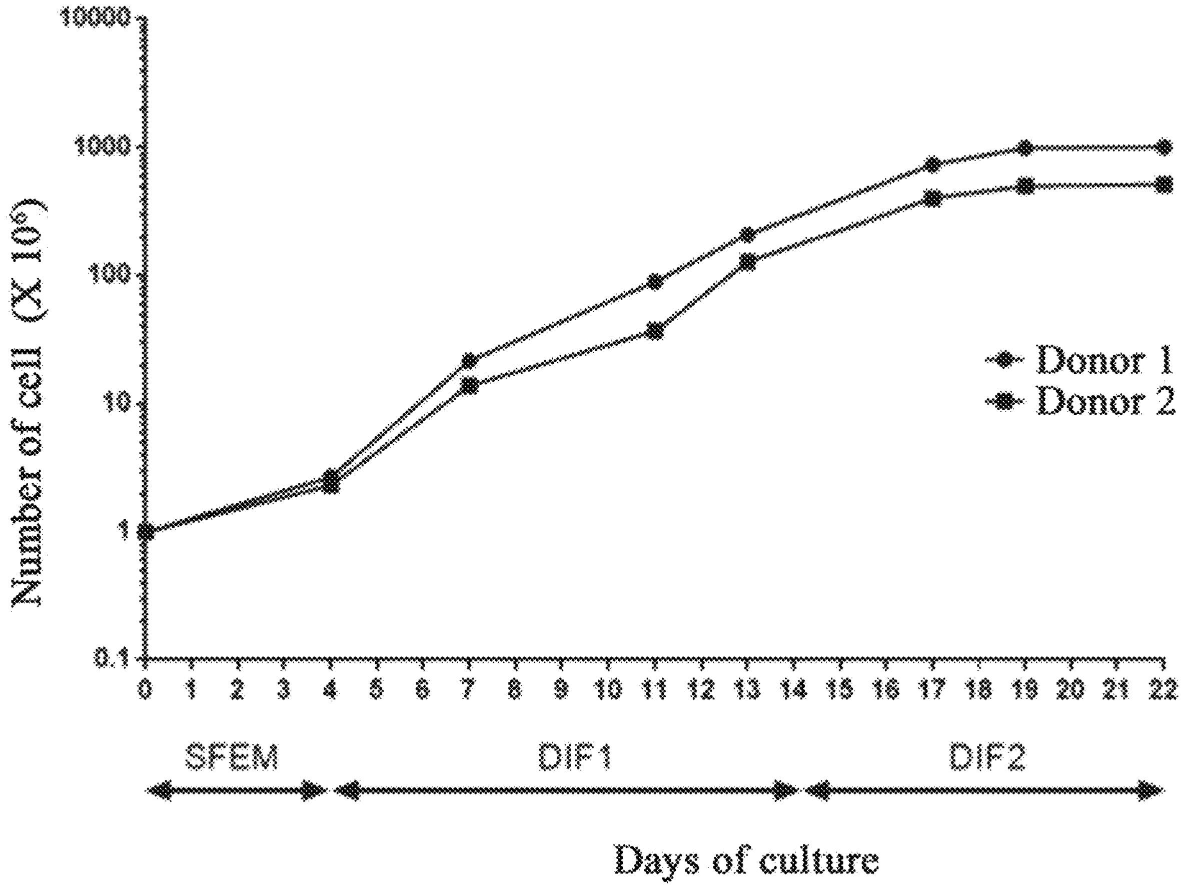
FIG. 2 is a cell proliferation curve of mature erythrocytes in vitro prepared from peripheral blood in Example 1 of the present invention. In the present invention, a comparison is made between the data of two donors.
Figure 3:
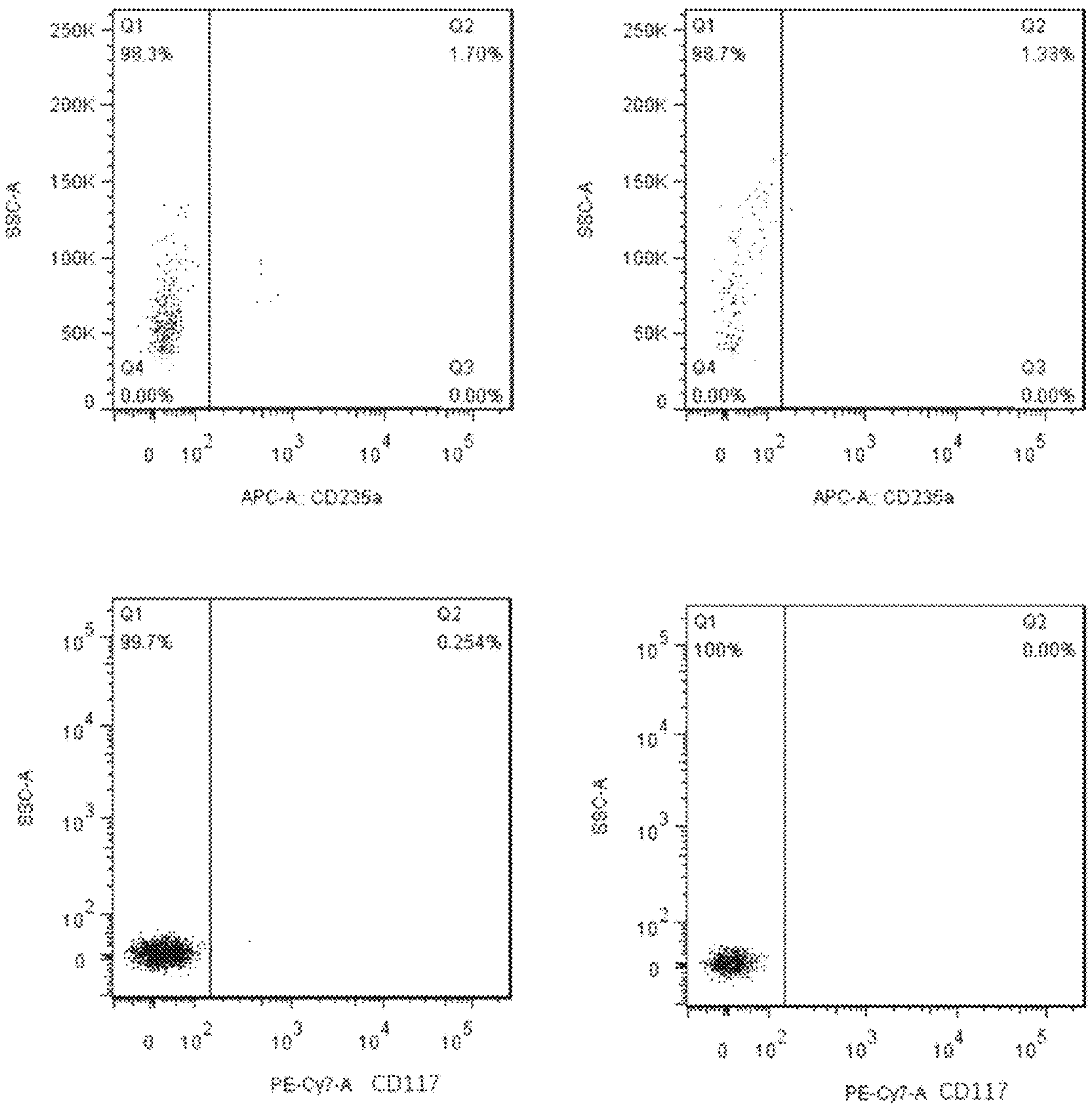
FIG. 3 is a schematic diagram showing the CD235a and CD117 expression levels of the two donors in the $Lin^{-}CD34^{-}$ cells enrichment stage.
Figure 4:
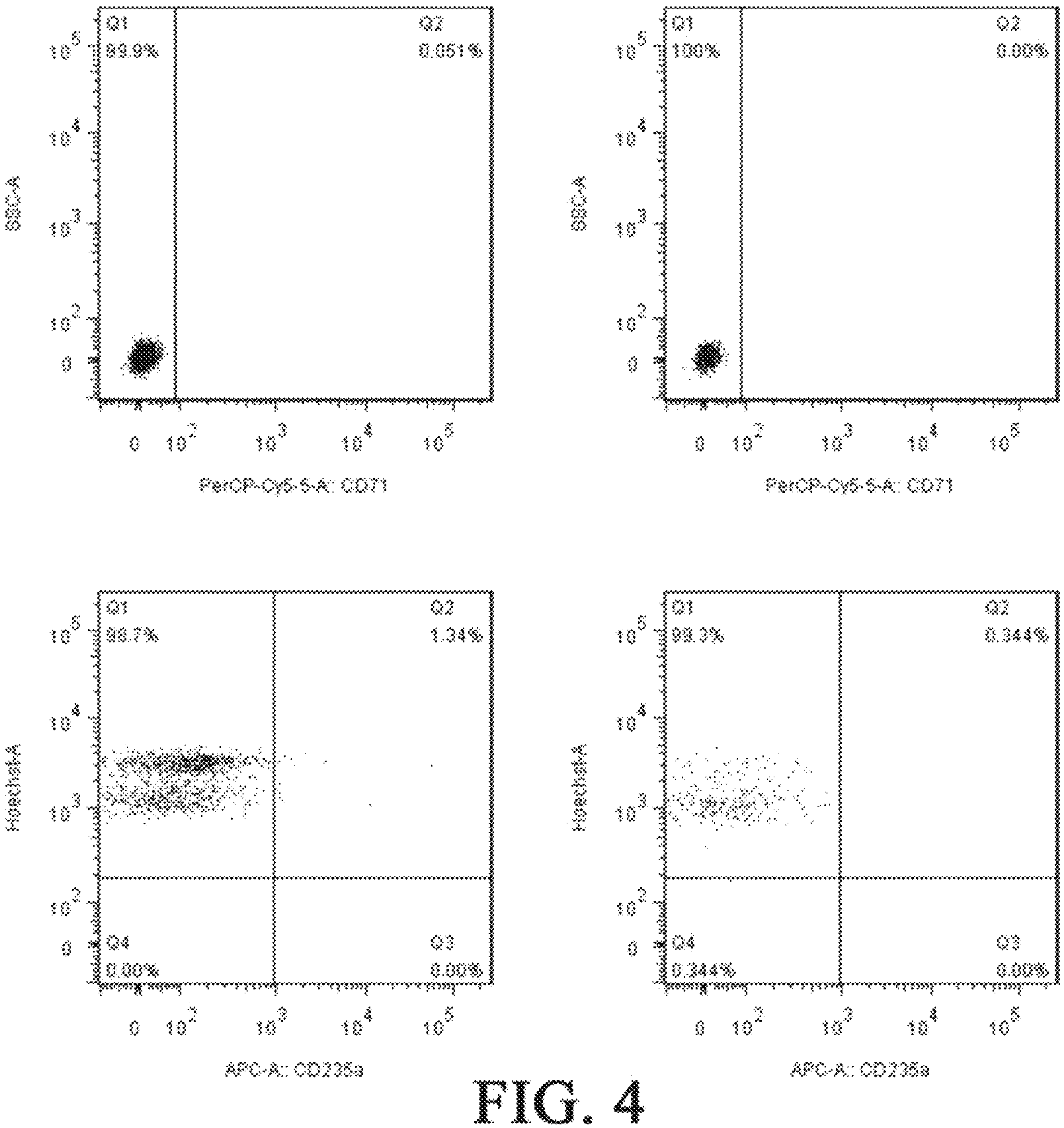
FIG. 4 is a schematic diagram showing the erythrocyte enucleation level identified after co-staining of the CD71 and hoechst33342/CD235a from the two donors in the $Lin^{-}CD34^{-}$ cells enrichment stage.
Figure 5:
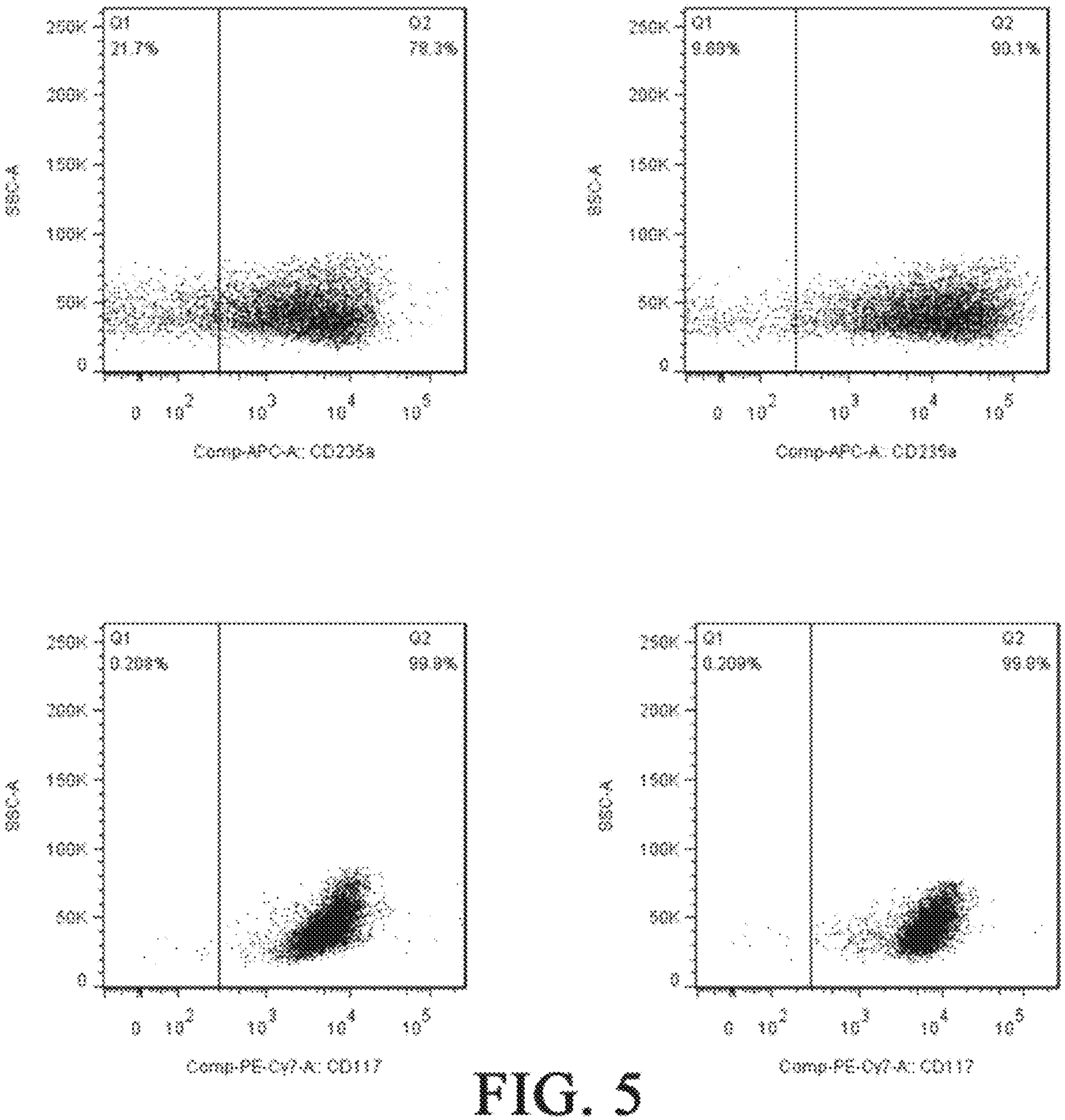
FIG. 5 is a schematic diagram showing the CD235a and CD117 expression level of the two donors in the $Lin^{-}CD34^{-}$ cell differentiation stage.
Figure 6:
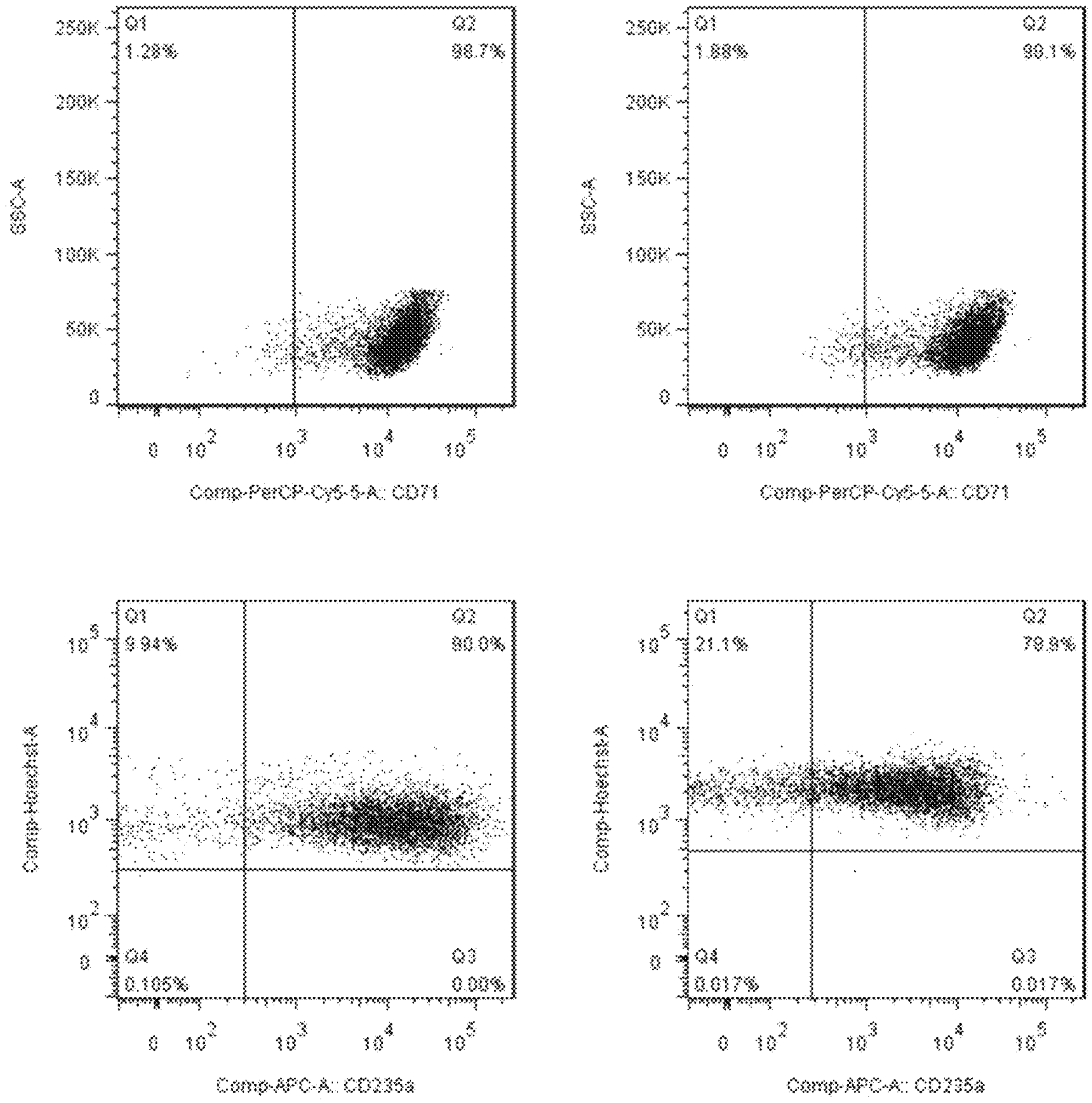
FIG. 6 is a schematic diagram showing the erythrocyte enucleation level identified after co-staining of the CD71 and hoechst33342/CD235a from the two donors in the $Lin^{-}CD34^{-}$ cell differentiation stage.
Figure 7:
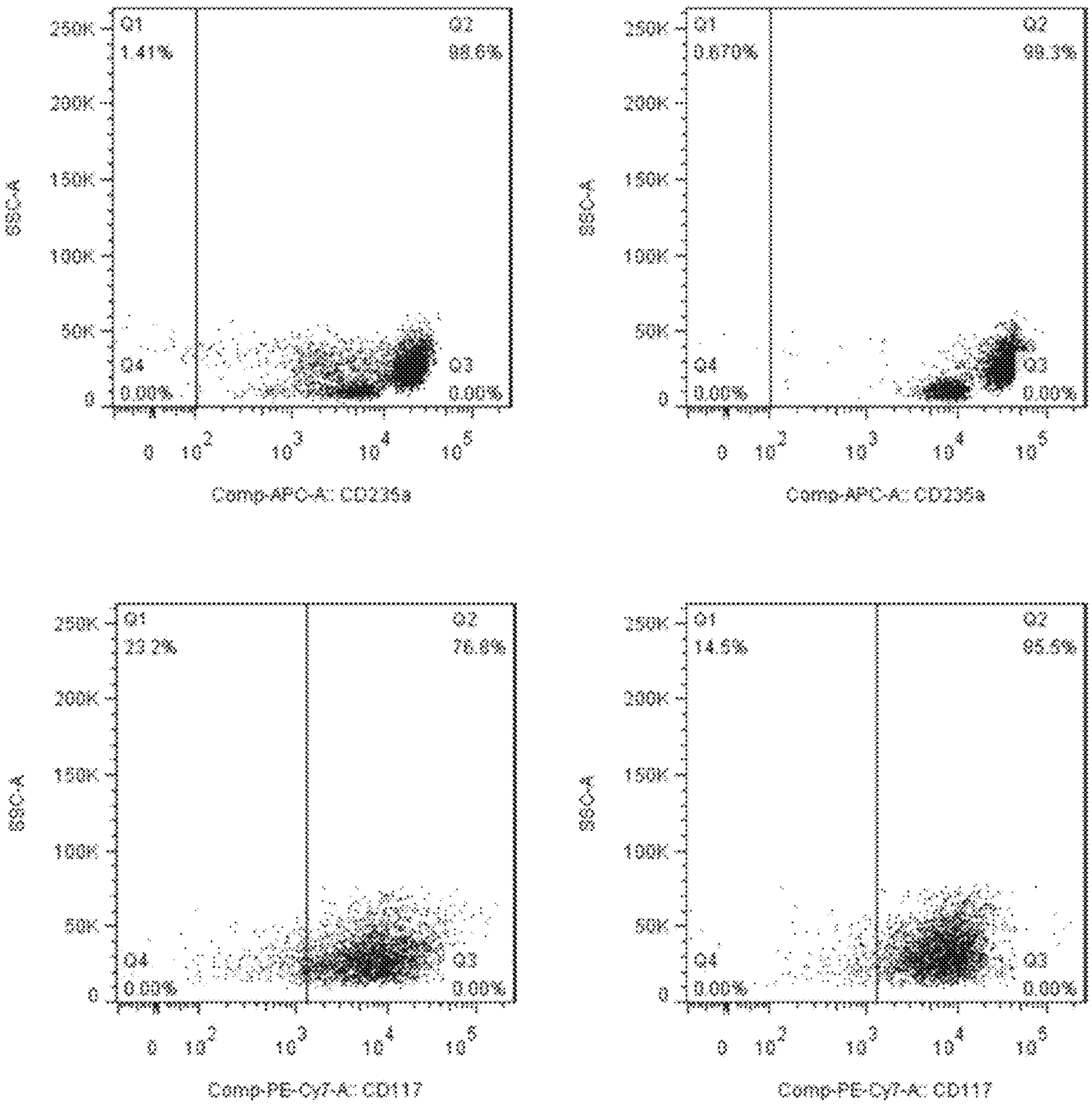
FIG. 7 is a schematic diagram showing the CD235a and CD117 expression level of the two donors in the mature stage of erythrocyte enucleation.
Figure 8:
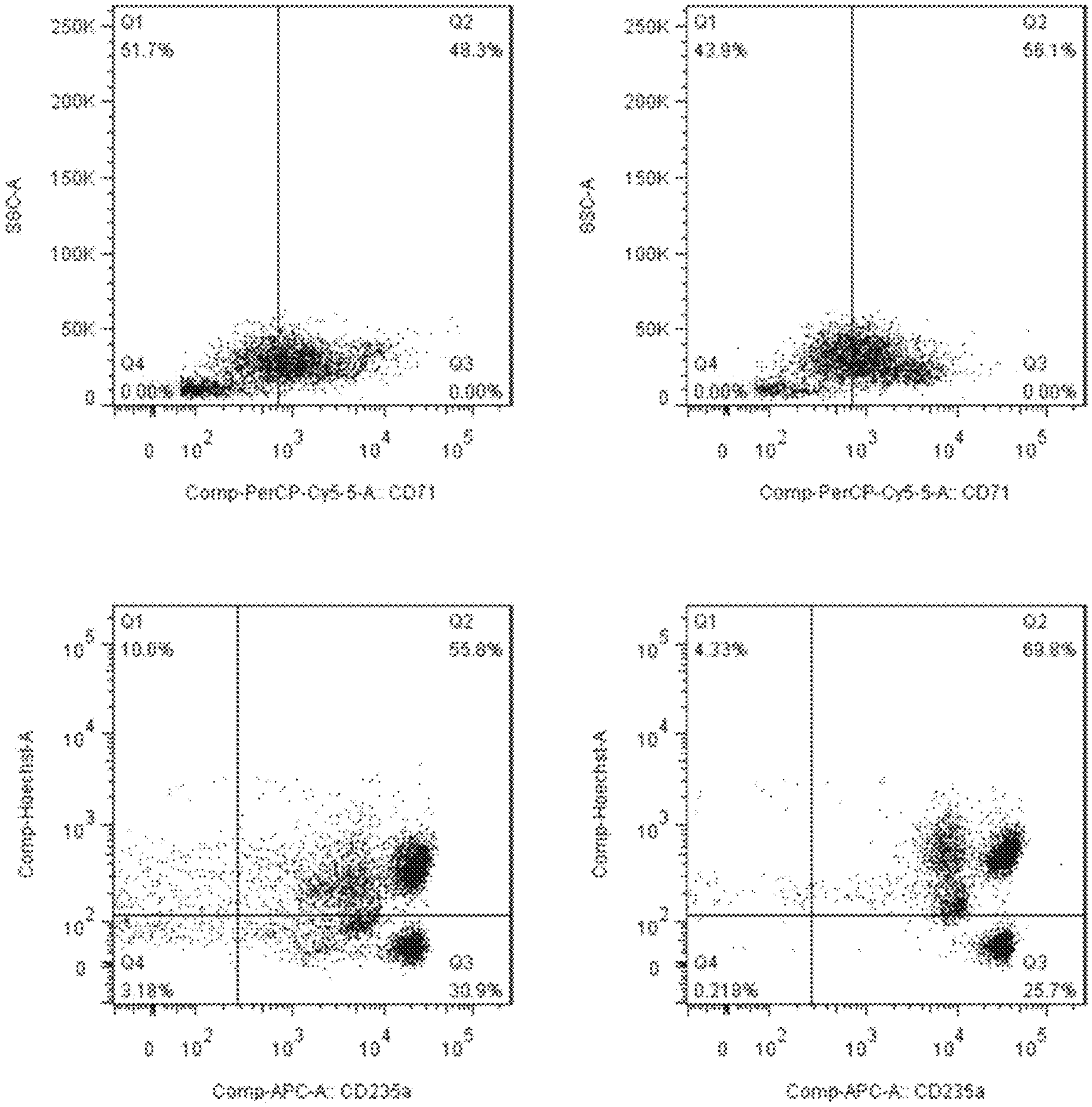
FIG. 8 is a schematic diagram showing the erythrocyte enucleation level identified after co-staining of the CD71 and hoechst33342/CD235a from the two donors in the mature stage of erythrocyte enucleation.
Figure 9:
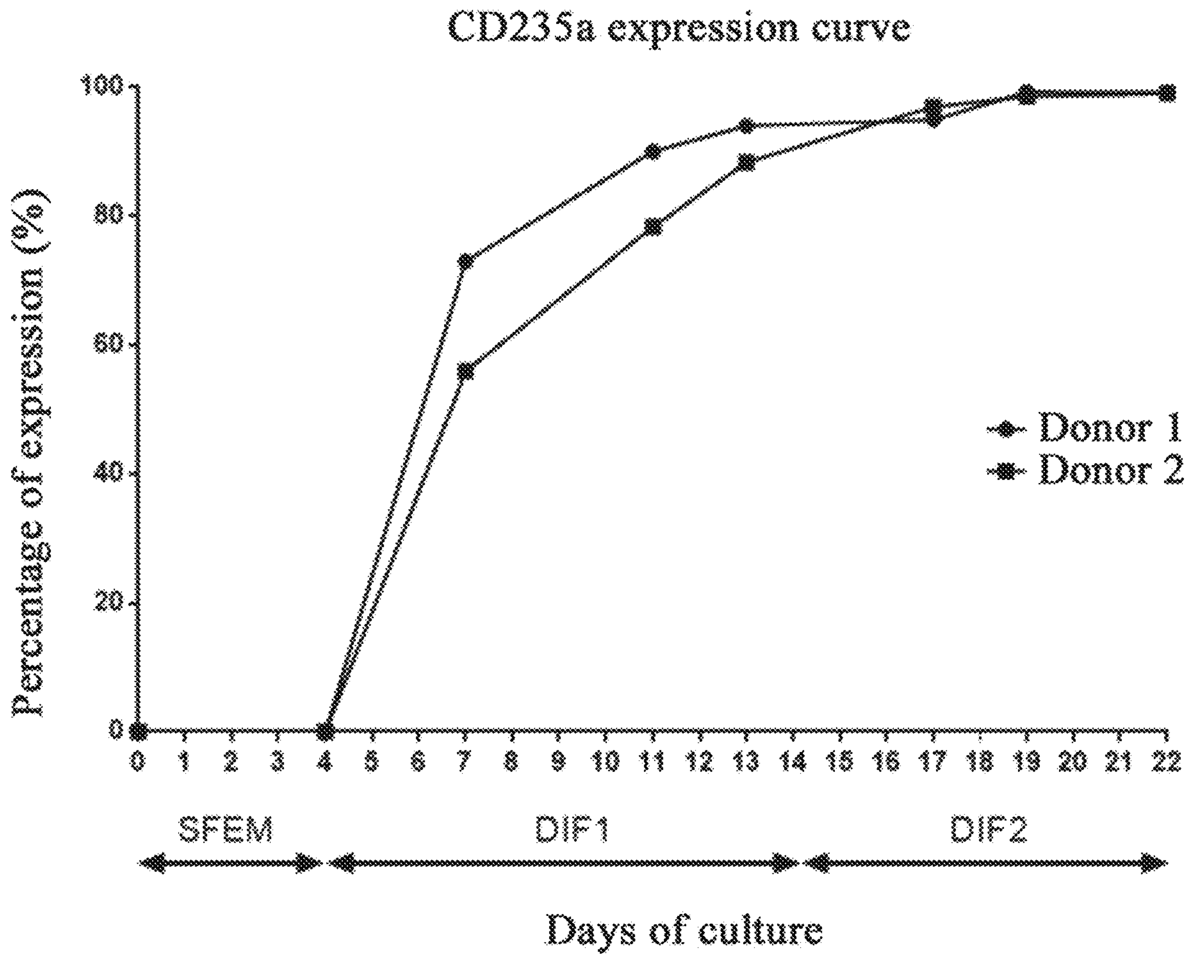
FIG. 9 is a curve showing a variation of cell CD235a expression in the differentiation culture stage.
Figure 10:
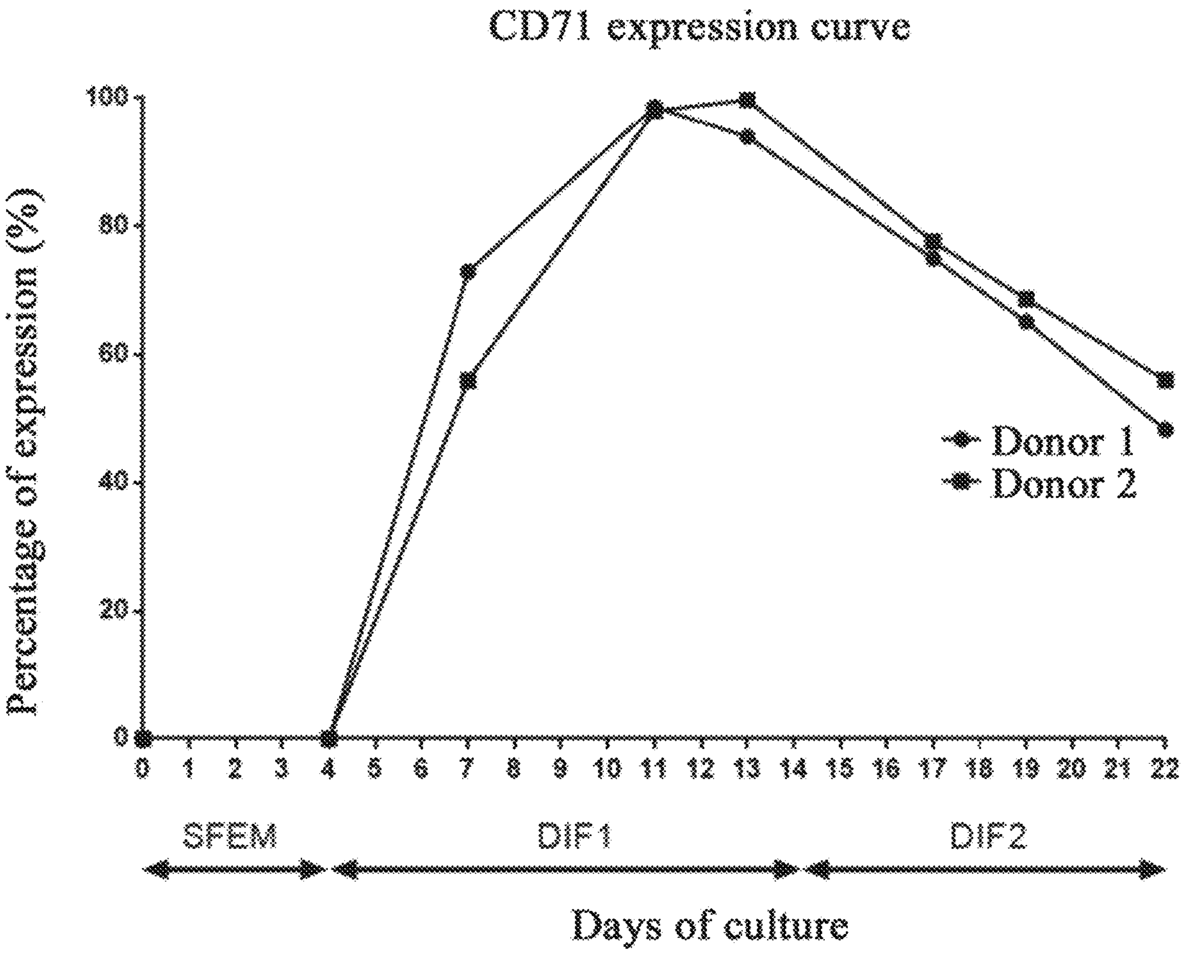
FIG. 10 is a curve showing a variation of cell CD71 expression in the differentiation culture stage.
Figure 11:
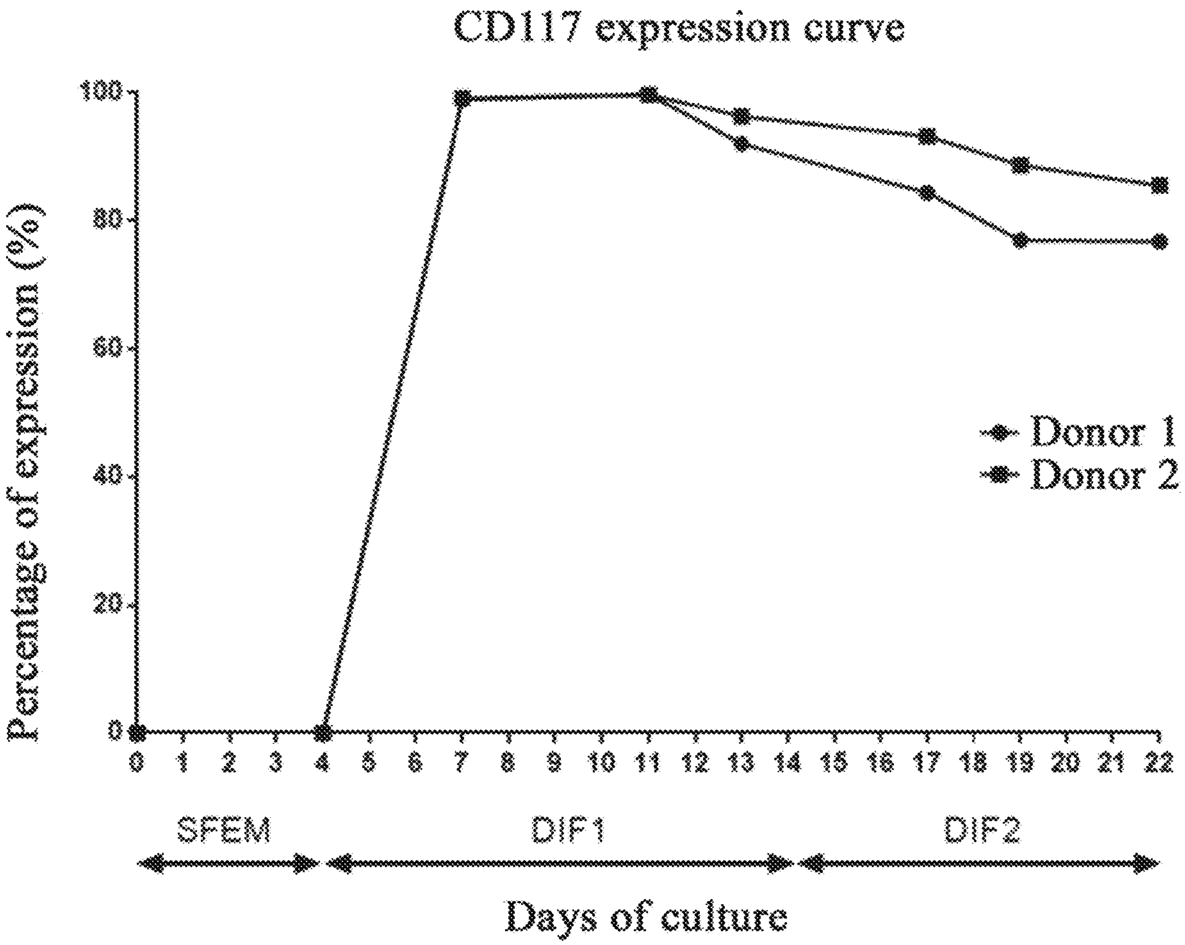
FIG. 11 is a curve showing a variation of cell CD117 expression in the differentiation culture stage.

To understand the objectives, technical solutions and advantages of the present invention more clearly, the present invention will be further described in detail with reference to the following specific embodiments and the accompanying FIGS. 1-20.

Technical terms in the technical solutions are introduced below:

Peripheral blood: peripheral blood refers to blood except for bone marrow; hematopoietic stem cells in bone marrow are clinically released to blood by some methods, and then are extracted and separated from the blood; and the stem cells obtained in this way are called peripheral blood stem cells.

Peripheral blood mononuclear cell: peripheral blood mononuclear cell refers to the cell having a mononuclear in peripheral blood, and includes lymphocyte and monocyte. At present, the major separation method of peripheral blood mononuclear cells is Ficoll-hypaque density gradient centrifugation method.

$Lin^{-}CD34^{-}$ cells: Lin cells refer to the cells not entering to each hematopoietic lineage for differentiation; $CD34^{-}$ cells refer to no CD34 surface marker expressed on the cell surface; and $Lin^{-}CD34^{-}$ cells refer to the cells not entering to each hematopoietic lineage for differentiation and not expressing a CD34-surface marker.

Biotin-labeled antibody: a biotin-labeled antibody is an antibody linked thereto a biotin; biotin-labeled reaction is simple, mild and rarely inhibits the antibody activity; the covalent binding between biotin and an antibody is a very simple and direct labeling method.

Hematopoietic stem cell proliferation medium: StemSpan™ SFEM serum-free amplification medium is a hematopoietic stem cell proliferation medium free of serum; after adding hematopoietic growth factors and/or other stimulating factors selected by user, the medium can promote the amplification of hematopoietic stem/progenitor cells (HSPC) or differentiation to a specific lineage.

Recombinant human fms-like tyrosine kinase 3 ligand (rhFIt3L): FMS-like tyrosine kinase 3 ligand (Flt-3 ligand) is also called FL, FIt3L, and FLT3LG, an α-helical cytokine that promotes the differentiation of multiple hematopoietic cell lineages. FLT3LG is homologous to the stem cell factor (SCF) and colony stimulating factor 1 (CSF-1) structurally. As a growth factor, FLT3LG increases the number of cells by activating hemopoietic progenitor cells.

Recombinant human stem cell factor (rhSCF): Kit ligand (KITLG) is also called a stem cell factor (SCF), and belongs to a type-I transmembrane glycoprotein of an SCF family. KITLG is a ligand of a receptor type protein tyrosine kinase KIT. SCF plays an important role in regulating cell survival and proliferation, hematopoiesis, maintenance of stem cells, cell development, migration and function.

Recombinant human interleukin 3 (rhIL-3): rhIL-3 is a glycoprotein belonging to a hematopoietic growth factor family, and shows multilineage activity in preclinical in vitro and in vivo study. With the aid of IL-3 protein, hemopoietic progenitor cells are proliferated and differentiated into mature erythrocyte, mastocyte, megakaryocyte and granulocyte.

Recombinant human interleukin 6 (rhIL-6): rhIL-6 is a multifunctional cytokine that regulates immune response, hematopoietic function, acute phase response and inflammatory response. rhIL-6 is synergic with IL-3 to accelerate the proliferation of hematopoietic cells.

Recombinant human erythropoietin (rhEpo): rhEpo is a major erythropoiesis factor and is synergic with various other growth factors (such as, IL-3, IL-6, glucocorticoid and SCF) used for developing into erythrocyte lineage from multipotential progenitor cells. Burst forming unit-erythroid (BFU-E): cells begin to express erythropoietin receptors and are sensitive to erythropoietin. It is an important erythroid hematopoietic cytokine.

Human transferrin (also called holo human transferrin: is a major Fe-containing protein in blood serum and can form a complex with iron ions for the generation of hemoglobin in erythrocyte.

Streptavidin: streptavidin is a secretory product in the culture process of *Streptomyces* avicllrdi, and is mainly extracted and purified by 2-iminobiotin affinity chromatography; 1 L of a culture solution contains 10-60 mg of the protein.

CD235a: also called glycophorin A, is a single-pass membrane glycoprotein expressed in mature erythrocytes and erythroid progenitor cells, and is a special marker protein on the surface of erythrocyte. CD235a expression indicates that the cell is differentiated into erythroid cell. A flow cytometry result analysis shows that in SFEM stage, cells do not express CD235a, indicating that the cells have not entered into erythroid differentiation. When the cells are changed the culture medium to a differentiation stage-1 culture medium, they are induced by cytokines in the medium and are differentiated into the erythroid and begin to express CD235a, and the proportion constantly increases with the differentiation time. After the cells are further changed to a differentiation stage-2 culture medium, since the cells have completely entered into the erythroid, almost all the cells express CD235a, indicating that almost all the cells are erythroid cells. The cell marker indicates that our differentiation system is successful in the induction process of erythroid cell culture in vitro.

CD117 is also called c-kit, and is SCF stem cell growth factor receptor, expressed on the surface of hematopoietic stem cells and other cells. SCF plays an important role in regulating cell survival and proliferation, hematopoiesis, maintenance of stem cells, cell development, migration and function. The variation in expression quantity of the receptor reflects the change in cell SCF-utilization ability. In SFEM condition, CD117 is not expressed, indicating that SCF is not utilized by Lin cells in the culture stage of SFEM. When the cells are placed in the differentiation stage-1 culture medium, the cells enter the erythroid differentiation, and the CD117 expression increases rapidly up to a peak; at this time, SCF is added to the medium to regulate cell survival and proliferation, hematopoiesis, maintenance of stem cells, and cell development. The cells enter into a mature decenucleation stage after placed in the differentiation stage-2 culture medium; and the CD117 expression gradually decreases.

CD71, a transferrin receptor 1, is a transmembrane glycoprotein consisting of two monomers linked via two disulfide bonds. Each monomer binds to a holo-transferrin molecule to produce a Fe-transferrin-transferrin receptor complex, and the complex enters into cells via endocytosis for the generation of hemoglobin in the process of developing into erythroid cells. CD71 does not expressed in SFEM condition, indicating that $Lin^-$ cells do not utilize transferrin in the culture stage of SFEM, and the cell does not enter into erythroid to take in Fe for hemoglobin synthesis. After placed in the differentiation stage-1 culture medium, the cells need to take in a large amount of transferrin for erythroid differentiation; therefore, the CD71 expression increases rapidly to satisfy the intake of cell transferrin. After placed in the differentiation stage-2 culture medium, the erythroid cell has synthesized enough hemoglobin; therefore, the CD71 expression gradually decreases and the erythrocyte trends to mature.

Hoechst33342 is a fluorescent dye used for DNA staining. The dye can pass through cell membrane and bind to DNA; if the cell is not denucleated, the dye binds to DNA and a positive signal can be detected by flow cytometry; if the cell is denucleated, a negative signal can be detected by flow cytometry.

Meanwhile, CD235a is a surface marker of erythrocyte; the co-expression of the two markers is simultaneously detected by flow cytometry; CD235a positive and Hoechst 33342 positive are non-denucleated erythroid cells, and CD235a positive and Hoechst 33342 negative are mature erythrocyte. In the SFEM culture medium and differentiation stage-1 culture medium, cells are subjected to erythroid differentiation from Lin cells, and the CD235a expression increases, but there is no enucleation; therefore, the cell is Hoechet 33342 positive. After placed in the differentiation stage-2 culture medium, the cells start to mature and denucleate, and Hoechst 33342 negative cells appear, indicating that erythrocyte is mature. The present invention cany perform morphology, structure and function identification on the mature erythrocyte.

GFP: green fluorescent protein. The protein is a fluorescent reporter gene which is fused with a desired gene anti-PD-1 scFv for constructing MSCV-anti-PD-1 scFv; the signal is detected to indicate that anti-PD-1 scFv is also expressed simultaneously. Therefore, GFP can serve as a detection signal to detect a desired gene. If GFP is positive, it indicates that the cell expresses anti-PD-1 scFv.

Example 1

I. Construction of an Anti-PD-1 scFv-Containing Lentiviral Vector

An anti-PD-1 single-chain variable region fragment (Anti-PD-1 scFv) was designed, wherein the Anti-PD-1 scFv had one or a combination of nucleotide sequences as shown in SEQ ID NO. 1-SEQ ID NO.6; synthesis was performed by a conventional biosynthesis method, and a vector construction was performed according to molecular cloning means; the Anti-PD-1 scFv was constructed in a lentiviral vector pCDH-MCS-T2A-copGFP-MSCV to obtain a vector of the desired sequence (MSCV-anti-PD-1 scFv), used for virus packaging.

II. Preparation of a Lentiviral Concentrate

The lentiviral package was performed using a ratio of MSCV-anti-PD-1 scFv: pSPAX2: VSVG=2:1:1. A 6-well plate was used in this Example, and plasmids were transfected into HEK 293T cells for virus packaging using a calcium phosphate transfection method with the vector of the desired sequence (MSCV-anti-PD-1 scFv): pSPAX2: VSVG=2 μg: 1 μg: 1 μg. The medium was changed 12 h after transfection to remove calcium phosphate, supernatant was collected respectively after 48 h and 72 h, and the cell culture supernatant was filtered with a 0.45 μm filter membrane. The collected and filtered cell culture supernatant was subjected to concentration by ultracentrifuging at a rotary speed of 70000RCF, time of 2 h and a temperature of 4° C. The supernatant was removed after centrifugation, and the remains were resuspended using the differentiation stage-1 culture medium; then quantified the virus titer using ELISA and stored at −80° C. for further use.

III. Obtaining $Lin^-CD34^-$ Cells from Peripheral Blood:

Whole blood was taken and diluted by a phosphate buffer solution in a ratio of 1:1, and then centrifuged for 15 min at 1200×g using a lymphocyte separation solution (Lymphoprep™, STEMCELL Technologies) and lymphocyte separation tube, then mononuclear cells were sucked out by a capillary.

The obtained peripheral blood mononuclear cells were centrifuged for 10 min at 300×g, and a phosphate buffer solution added with 2% bovine serum albumin and 1 mM EDTA as a cell separation buffer solution was used to resuspend the cells in a ratio of $1\times10^6$ cells/ml to obtain a cell suspension.

Biotin-labeled antibodies (as shown in Table 1) were diluted by the cell separation buffer solution which was 10 times volume of the cell suspension. The biotin-labeled antibodies were added to the cell suspension to 20-40 μg/ml, then 300 μl streptavidin-labeled magnetic beads were added, and incubation was performed for 30 min at 4° C.; afterwards, the solution was placed in a magnetic stand for 6-8 min for the separation of lineage cells. The non-adsorbed separation buffer solution was collected, centrifuged for 10 min at 300×g to obtain $Lin^-CD34^-$ cells.

TABLE 1

Ingredients of 1 ml biotin-labeled antibodies

| Ingredients | Volume |
| --- | --- |
| Biotin-labeled murine anti-human CD3 antibody | 20 ul |
| Biotin-labeled murine anti-human CD14 antibody | 20 ul |
| Biotin-labeled murine anti-human CD16 antibody | 20 ul |

TABLE 1-continued

| Ingredients of 1 ml biotin-labeled antibodies | |
|---|---|
| Ingredients | Volume |
| Biotin-labeled murine anti-human CD19 antibody | 20 ul |
| Biotin-labeled murine anti-human CD41a antibody | 20 ul |
| Biotin-labeled murine anti-human CD56 antibody | 20 ul |
| Biotin-labeled murine anti-human CD235a antibody | 20 ul |

IV. Enrichment of $Lin^{-}CD34^{-}$ Cells:

0.1-0.5×105 $Lin^{-}CD34^{-}$ cells were inoculated into a hematopoietic stem cell proliferation medium on day 0; a combination of cytokines and penicillin-streptomycin were added. The hematopoietic stem cell proliferation medium, the combination of cytokines and penicillin-streptomycin formed an enrichment cell culture medium, having the ingredients as shown in Table 2. Culture was performed till day 4, and the stage was defined as a $Lin^{-}CD34^{-}$ cells enrichment stage.

Infection method: the cells were resuspended in the differentiation stage-1 culture medium at a cell density of $1\times10^{6}$. The infection volume and virus dosage were calculated, and the virus dosage was calculated to obtain a final concentration of $5\times10^{7}$ TU/ml-$5\times10^{8}$ TU/ml; in terms of the infection volume, polybrene was added to the lentiviral concentrate in the amount of 10 μg/ml; mixed and incubated for 5 min. The incubated lentiviral concentrate was added to the cells and mixed thoroughly. The infection of cells was performed by centrifugation using a horizontal rotor centrifugal machine, with a rotary speed of 500×g, a temperature of 32° C. and a time of 90 min. After centrifugation, the cells were cultured under conditions of 37° C. and 5% $CO_2$.

In the differentiation stage-1 culture medium, only cytokines associated with the development towards erythroid were provided, to ensure the proliferation and differentiation of $Lin^{-}CD34^{-}$ cells towards erythroid. Meanwhile, the virus infection was performed during the fastest proliferation and differentiation stage of said cells, to ensure the introduction of the desired gene (anti-PD-1 scFv) and the expression thereof onto cell membranes.

TABLE 2

| Ingredients required in the preparation of 1 L enrichment cell culture medium: | | | |
|---|---|---|---|
| Ingredients | Concentration of a stock solution | Final concentration | Volume |
| StemSpan serum-free medium (STEMCELL Technologies) | 1× | 1× | 1 L |
| Recombinant human fms-like tyrosine kinase 3 ligand (FIt3L) | 200 mM | 2 mM | 10 ml |
| Recombinant human stem cell factor (SCF) | 100 μg/ml | 100 ng/ml | 1 ml |
| Recombinant human interleukin 3 (IL-3) | 100 μg/ml | 100 ng/ml | 1 ml |
| Recombinant human interleukin 6 (IL-6) | 800 μg/ml | 800 pg/ml | 1 ul |

V. Induction of the $Lin^{-}CD34^{-}$ Cells to Differentiate into Erythroid and Performing Proliferation Thereon The culture system was changed on day 5, and the medium was changed to a differentiation stage-1 culture medium (as shown in Table 3), then proliferation culture was performed at 37° C. and 5% $CO_2$ conditions.

TABLE 3

| Ingredients required in the preparation of 1 L differentiation stage-1 culture medium | | |
|---|---|---|
| Ingredients | Final concentration | Volume |
| IMDM | 85% | 850 ml |
| Fetal bovine serum (FBS, Gibco) | 10% | 100 ml |
| Human plasma (Plasma) | 5% | 50 ml |
| Glutamine | 2 nM | 10 |
| Bovine serum albumin | 2% | 20 ml |
| Human transferrin | 500 μg/ml | 100 |
| Recombinant human insulin | 10 μg/ml | 100 μl |
| Penicillin-Streptomycin | 2% | 20 ml |
| Recombinant human interleukin 3 | 100 ng/ml | 1 ml |
| Recombinant human erythropoietin | 100 ng/ml | 1 ml |
| Recombinant human stem cell factor | 100 ng/ml | 1 ml |

VI. Infection of $Lin^{-}CD34^{-}$ Cells with a Lentiviral Concentrate

On day 6, the cells were infected with MSCV-anti-PD-1 scFv prepared previously and cryopreserved at −80° C.

VII. Erythrocyte Enucleation to Obtain Mature Anti-PD-1 scFv Erythrocytes

The culture system was changed on day 14. The medium was changed to a differentiation stage-2 culture medium (as shown in Table 4), then the cells were placed under conditions of 37° C. and 5% $CO_2$ for culture till day 22, thus genetically engineered erythrocytes carrying the anti-PD-1 single chain antibody were obtained; and the stage was defined as a mature stage of erythrocyte enucleation. During the whole periods of 0-22 days, the medium was changed every 2-4 days to one corresponding the culture stage thereof.

TABLE 4

| Ingredients required in the preparation of 1 L differentiation stage-2 culture medium: | | |
|---|---|---|
| Ingredients | Final concentration | Volume |
| IMDM | 85% | 850 ml |
| Fetal bovine serum (FBS, Gibco) | 10% | 100 ml |
| Human plasma (Plasma) | 5% | 50 ml |
| Glutamine | 2 mM | 10 ml |
| Bovine serum albumin | 2% | 20 ml |
| Human transferrin | 500 μg/ml | 100 μl |
| Recombinant human insulin | 10 μg/ml | 100 μl |
| Penicillin-Streptomycin | 2% | 20 ml |
| Recombinant human erythropoietin | 2 U/ml | 20 ul |

VIII. Identification and Detection of Erythrocytes (I) Analysis on the Quantity of Cell Proliferation:

The quantity of cells was respectively detected from the day 0 to day 22. The cells in the culture system were fully resuspended every 3-4 days; 10 μl cell suspension was mixed with 10 μl Trypan Blue Dye, and cells were counted using a cell counter.

Specifically, the cell proliferation profiles were as follows, and the quantity of starting cells was normalized to $1\times10^6$ at this time:

| | Day | | | | | | | |
|---|---|---|---|---|---|---|---|---|
| | 0 | 4 | 7 | 11 | 13 | 17 | 19 | 22 |
| Donor 1 | 1 | 2.69 | 21.53 | 89.20 | 209.17 | 738.24 | 996.62 | 1011.38 |
| Donor 2 | 1 | 2.33 | 13.84 | 36.91 | 126.73 | 406.03 | 501.92 | 517.22 |

The obtained quantities of cells were plotted into a cell proliferation curve, as shown in FIG. 1. It can be seen that erythrocyte can achieve normal proliferation and differentiation in such culture conditions, and effect 1000 times of proliferation.

(II) Cell Phenotype Analysis:

The cells were taken respectively from the $Lin^-CD34^-$ cells enrichment stage, the $Lin^-CD34^-$ cells differentiation stage, and the mature stage of erythrocyte enucleation for analysis, and the specific operating process was as follows.

The cells in the culture system were fully resuspended, and 50-100 μl cell suspension was taken and added to 500 μl phosphate buffer solution. 0.5 μl murine Anti-human CD235a APC antibody (mouse Anti-human CD235a APC), 2 μl murine Anti-human CD71-PerCP Cy5.5 antibody (mouse Anti-human CD71-PerCP Cy5.5), 2 μl murine Anti-human CD117-PE Cy7 antibody (mouse Anti-human CD117-PE Cy7), and 0.5 μl Hoechst 33342 dye were respectively added and mixed thoroughly, then incubated for 20 min in the dark. The cells were detected by a flow cytometry. An analysis was performed on the expression levels of specific surface markers of cells of interest. A variation curve was plotted in terms of the analysis at different time points, to obtain the schematic diagrams as shown in FIGS. 2-11.

(III) Analysis on the Erythrocyte Enucleation:

A proportion of the CD235a positive cells/Hoechst 33342 negative cells was analyzed via flow cytometry, and the proportion can reflect the enucleation of the cells.

Figure 12:
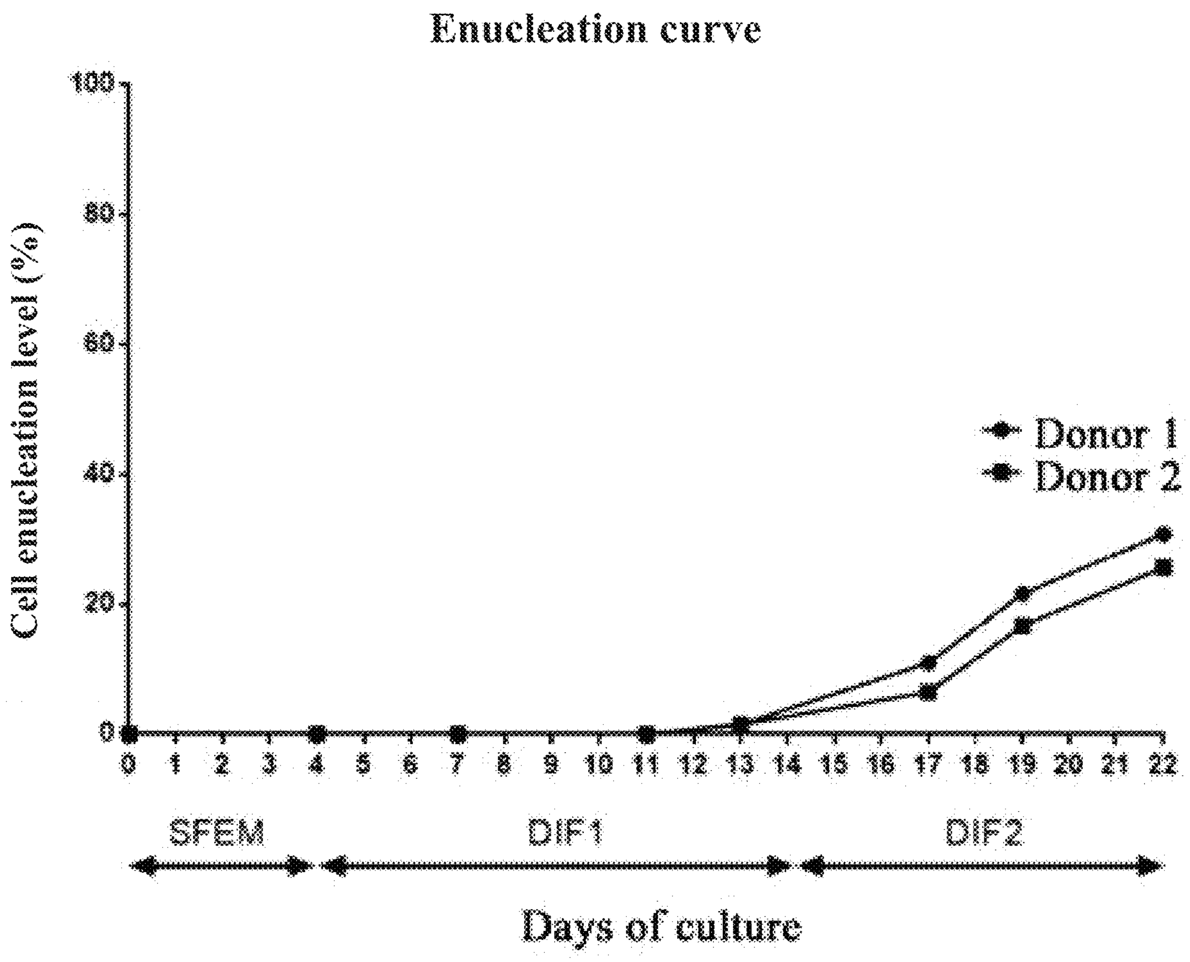
FIG. 12 is a curve showing erythrocyte enucleation during preparation.

The schematic diagram as shown in FIG. 12 was obtained. As shown in the figure, the enucleation level of the cells began to improve significantly from the 13rd day.

(IV) Cell Morphology Analysis:

$0.5\text{-}1\times10^6$ cells were taken and subjected to centrifugation and smear using a hemocyte centrifugation-smear machine.

The cells were fixed at room temperature for 2 min using a −20° C. pre-cooled methanol.

The fixed blood smear was washed for 3 times with water, 5 min each time, and then placed at room temperature for air drying.

10 ml phosphate buffer solution was used to dissolve a benzidine tablet (Benzidine, Sigma), and 10 μl hydrogen peroxide solution was added, and filtering was performed. 300-500 μl of the solution was used to stain the blood smear for 1 h at room temperature.

The stained blood smear was washed for 3 times with water, 5 min each time, and then placed at room temperature for air drying.

A Giemsa stain solution was used to secondarily stain the blood smear for 35-40 min at room temperature.

The stained blood smear was washed for 3 times with water, 5 min each time, and then placed at room temperature for air drying.

The blood smear was sealed with a sealing agent, observed and taken pictures under the microscope.

Figure 13:
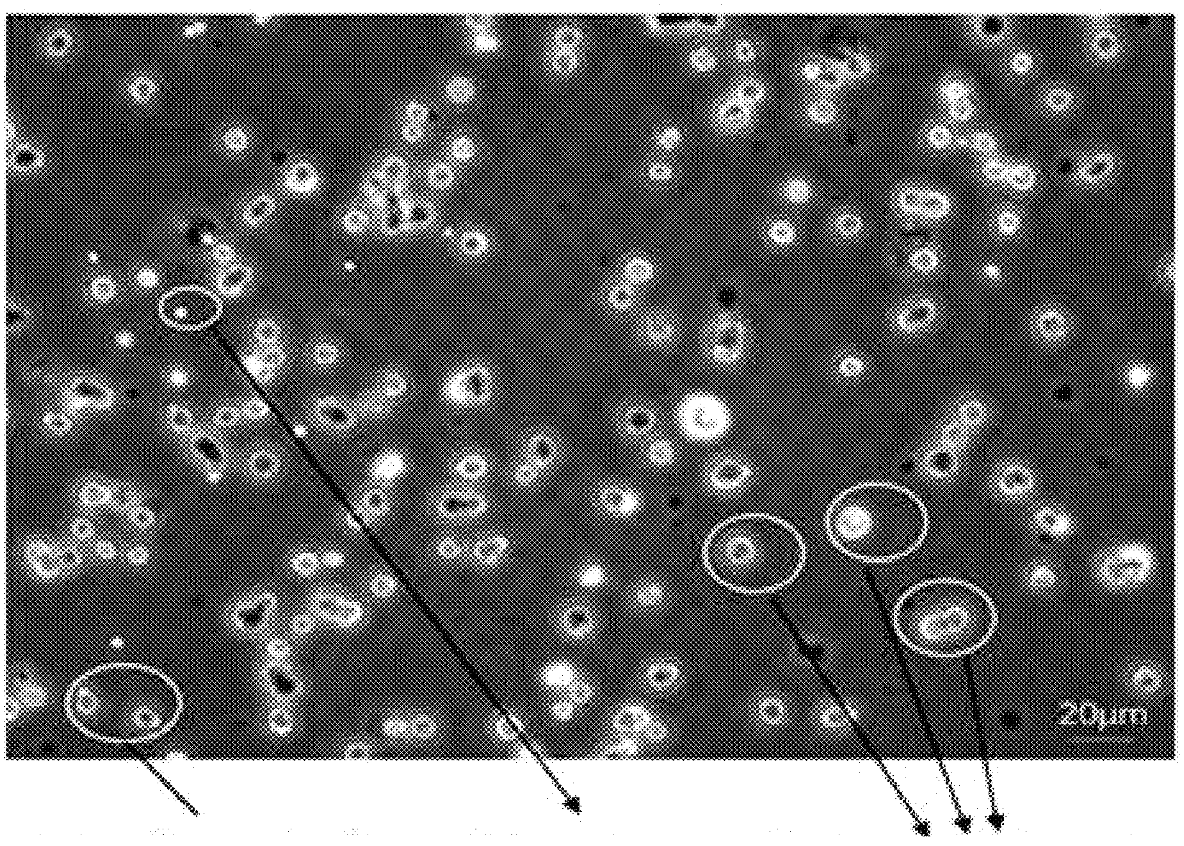
FIG. 13 shows an erythrocyte morphology examined under a microscope by smearing and staining the cells obtained after differentiation provided by a donor 1.
Figure 14:
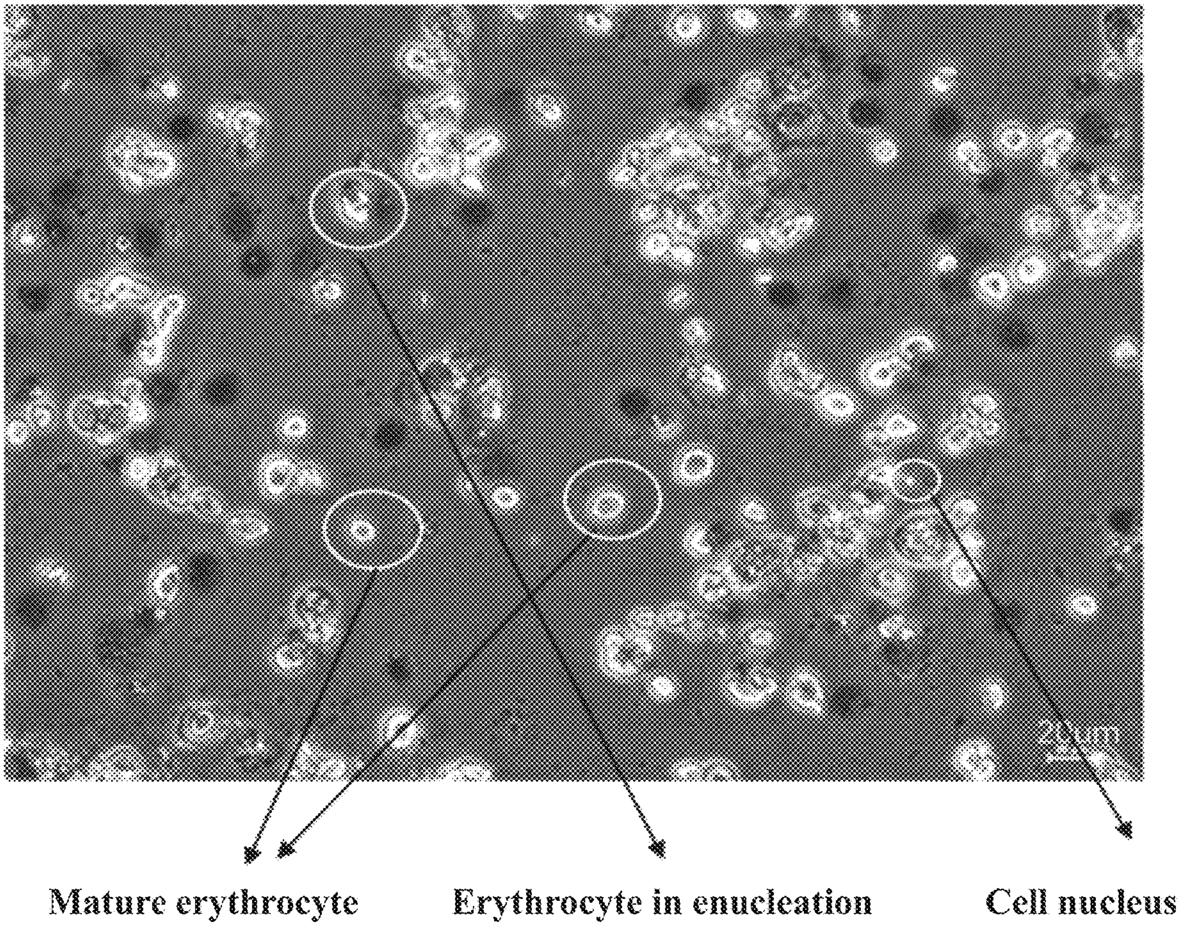
FIG. 14 shows an erythrocyte morphology examined under a microscope by smearing and staining the cells obtained after differentiation provided by a donor 2.

The schematic diagrams were as shown in FIG. 13 and FIG. 14. It can be seen from the figures that after the completion of cell differentiation on day 22, mature erythrocytes significantly appeared.

IX. Detection and Identification of the Genetically Engineered Erythrocytes Carrying the Anti-PD-1 Single Chain Antibody (I) Detection on the Transformation Efficiency of Anti-PD-1 scFv Using a Luciferase GFP gene was constructed downstream of the desired fragment (anti-PD-1 scFv), such that the desired sequence fragment had a luciferase reporter gene. GFP fluorescence was used to indicate the expression of anti-PD-1 scFv in erythrocytes, thus judging the transformation efficiency of anti-PD-1 scFv. The anti-PD-1 scFv erythrocytes were respectively placed under a normal light source and a GFP fluorescent protein excitation light source for microscopic examination.

Figure 15:
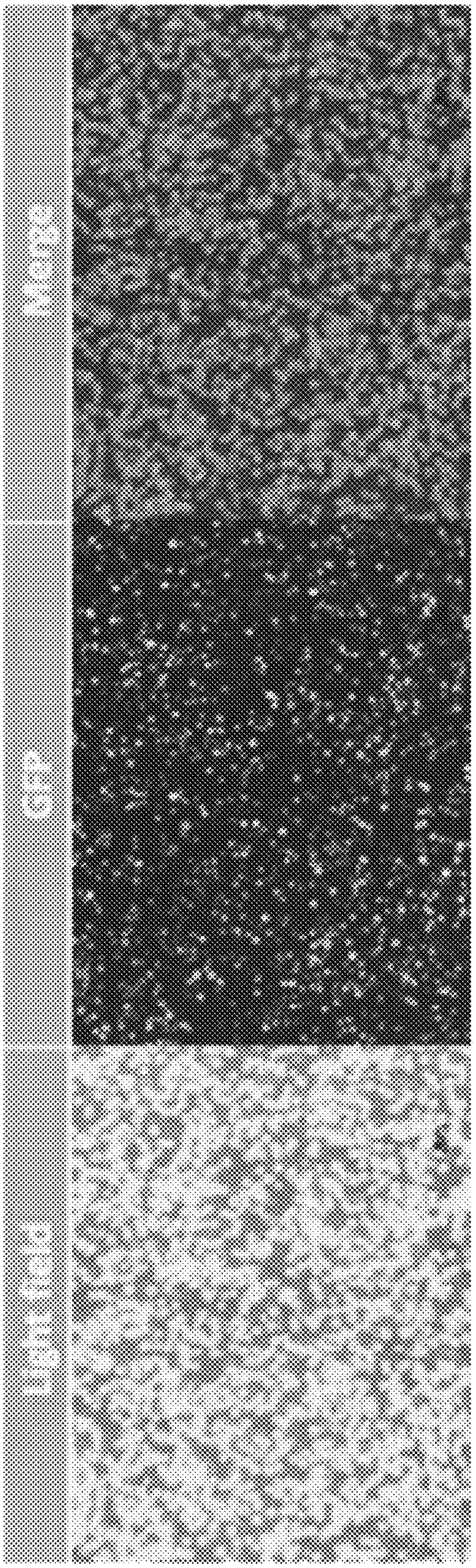
FIG. 15 shows a diagram of a transformation efficiency of anti-PD-1 scFv detected by a luciferase.

FIG. 15 showed the transformation efficiency of anti-PD-1 scFv detected by luciferase. The "Light field" in the figure represented a microscope photograph of anti-PD-1 scFv erythrocytes under a light field (normal light source); "GFP" represented a microscope photograph of anti-PD-1 scFv erythrocytes under the GFP fluorescent protein excitation light source; "Merge" represented the effect image obtained by overlapping the microscope photograph of anti-PD-1 scFv erythrocytes under the light field and the microscope photograph of anti-PD-1 scFv erythrocytes under the GFP fluorescent protein excitation light source. As shown in the figure, the Lin cells in peripheral blood was subjected to genetic engineering modification, and GFP served as a reporter gene; the anti-PD-1 scFv erythrocytes accounted for 95% of the total cells, indicating that the genetic engineering modification had an efficiency of more than 95%.

(II) Detection of the Expression Efficiency of Anti-PD-1 scFv in Erythrocyte by Flow Cytometry A proportion of the CD235a positive cells/GFP positive cells was analyzed via flow cytometry, and the proportion can reflect the expression efficiency of anti-PD-1 scFv in erythrocytes.

Figure 16:
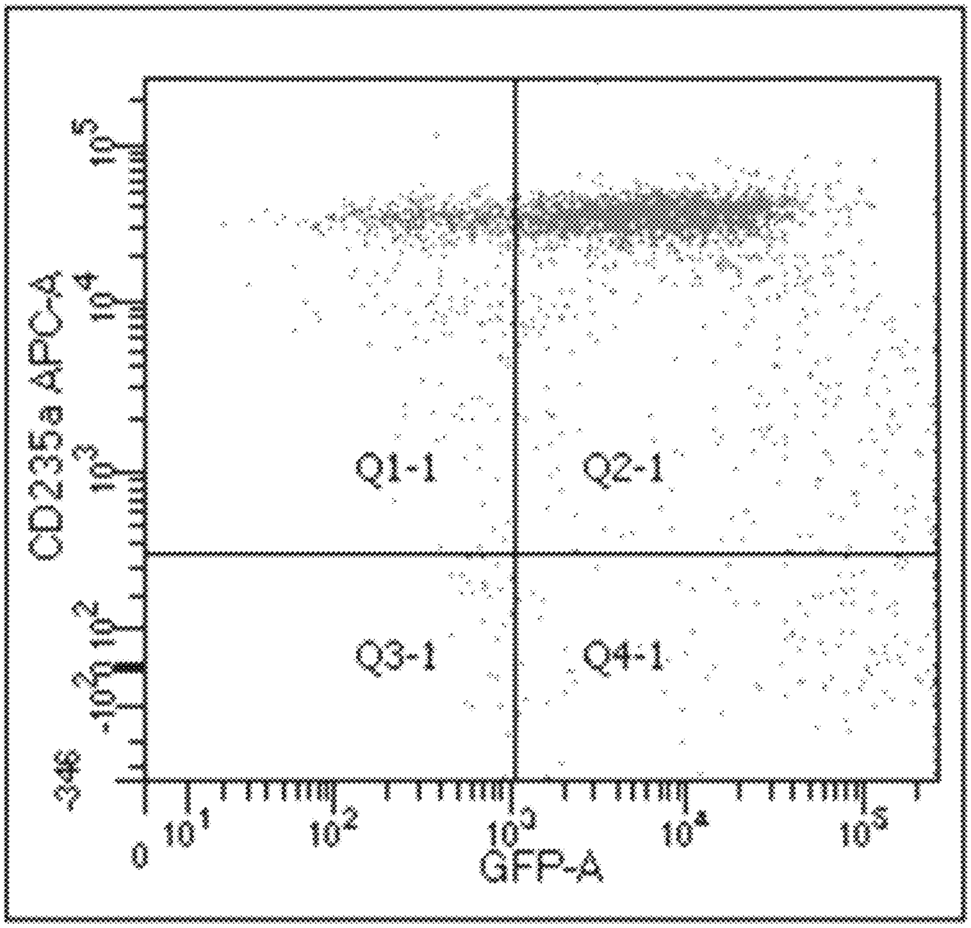
FIG. 16 shows a diagram of an expression efficiency of anti-PD-1 scFv in erythrocyte detected by flow cytometry.

As shown in FIG. 16, after anti-PD-1 scFv erythrocytes became mature erythrocytes at the end of differentiation, about 85% of the cells are still GFP-positive, indicating that at the end of differentiation the anti-PD-1 scFv erythrocytes were still high-level expression of anti-PD-1 scFv having immune activation ability.

(III) Detection of the Distribution of Anti-PD-1 scFv Erythrocytes in Mice Dir Staining Experiments Dir-stained erythrocytes were injected into the tail veins of mice, and the distributions of erythrocytes in mice bodies were subjected to living imaging detection at different time points (1.5 h/4 h/5 h/24 h), and 5 days later, the mice were sacrificed and subjected to tissue and organ imaging detection, to obtain the distributions of erythrocytes in mice organs.

Figure 17:
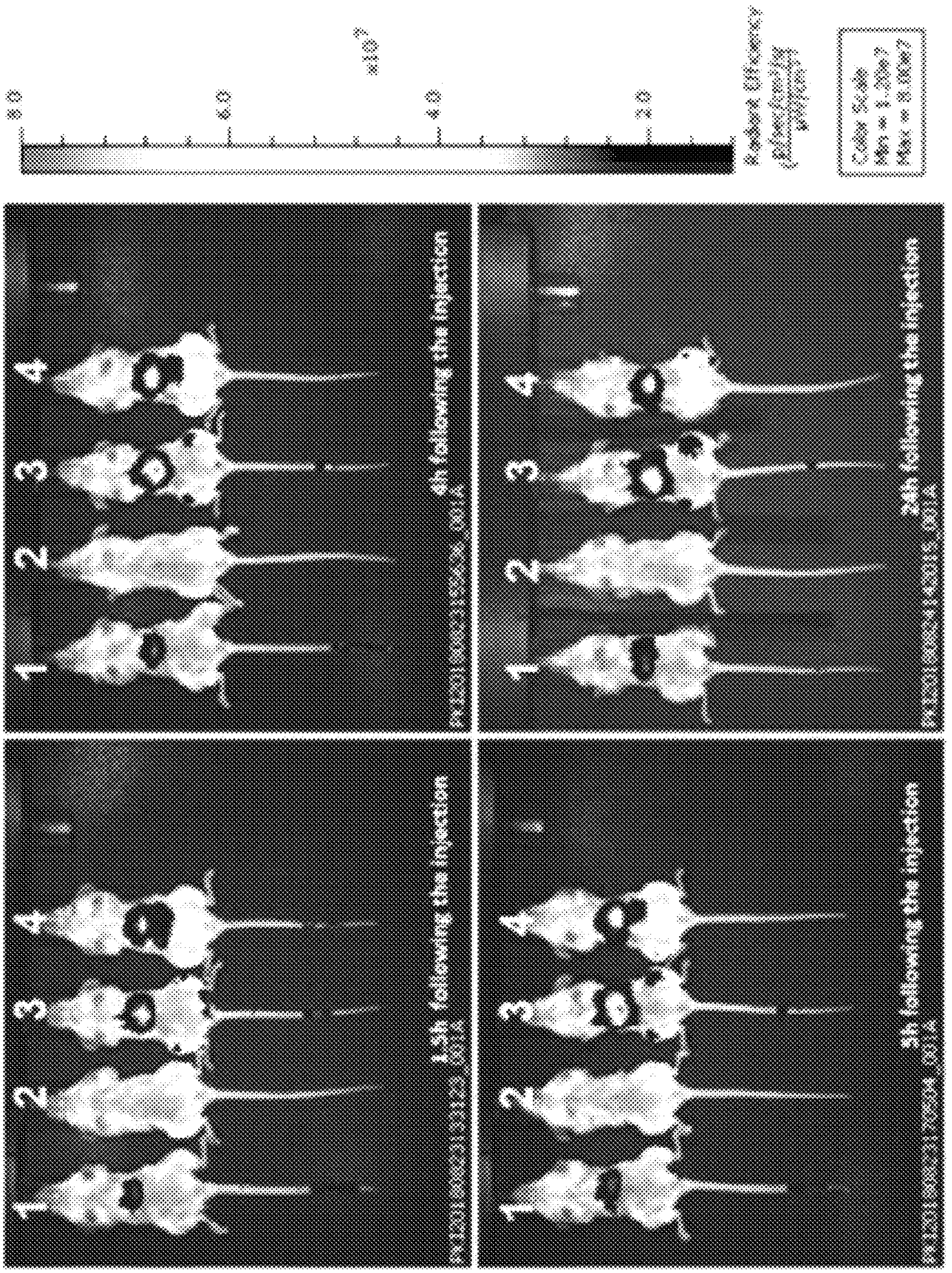
FIG. 17 shows a distribution diagram of anti-PD-1 scFv erythrocytes in a mouse body.
Figure 18:
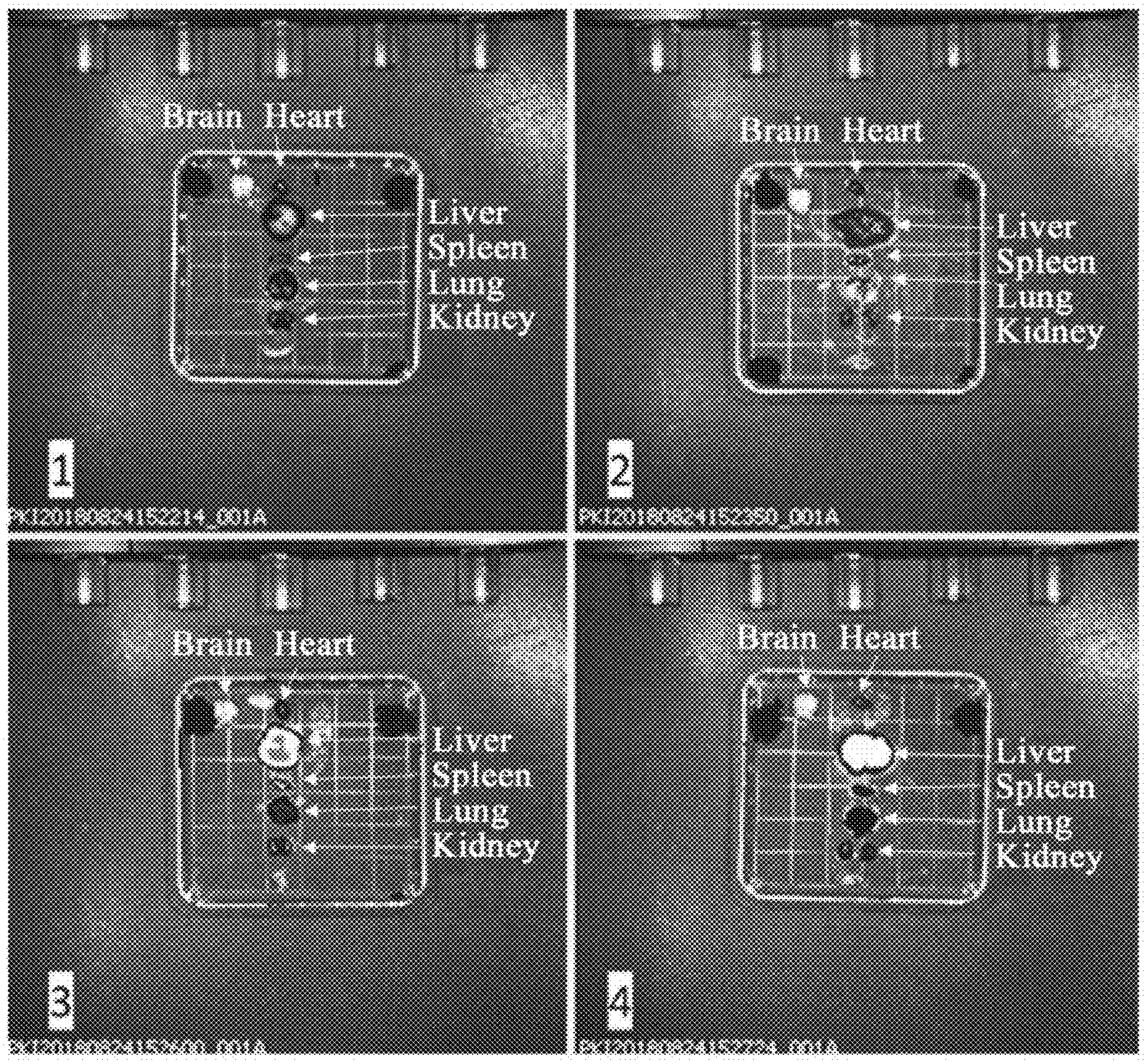
FIG. 18 is a diagram showing distribution of anti-PD-1 scFv erythrocytes in organs of a mouse body.

FIG. 17 showed the distribution diagrams of anti-PD-1 scFv erythrocytes in mice bodies; FIG. 18 showed the distribution diagrams of anti-PD-1 scFv erythrocytes in mice organs. In the figures, mouse No. 1 was tail-intravenously injected with a Dir staining solution; mouse No. 2 was tail-intravenously injected with normal erythrocytes not stained with Dir; mouse No. 3 was tail-intravenously injected with normal erythrocytes stained with Dir; and mouse No. 4 was tail-intravenously injected with anti-PD-1 scFv erythrocytes stained with Dir. As shown in FIGS. 17-18, the distribution of the anti-PD-1 scFv erythrocytes and normal erythrocyte in mice (including organs) is consistent.

(III) In Vitro T Cell Activation Function Experiment

The anti-PD-1 scFv erythrocytes and T cells were co-cultured to detect the activation function of the anti-PD-1 scFv erythrocytes to T cells.

Figure 19:
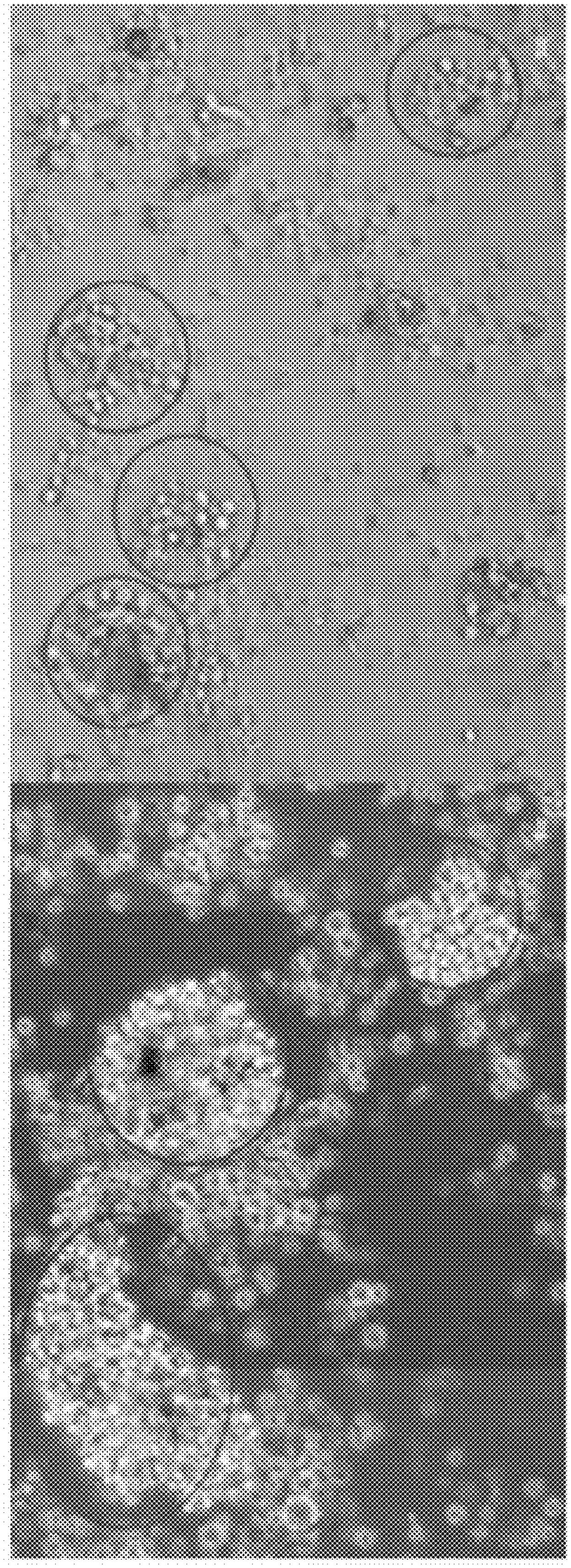
FIG. 19 is a microscope examination diagram showing co-culture of anti-PD-1 scFv erythrocytes and T cells.
Figure 20:
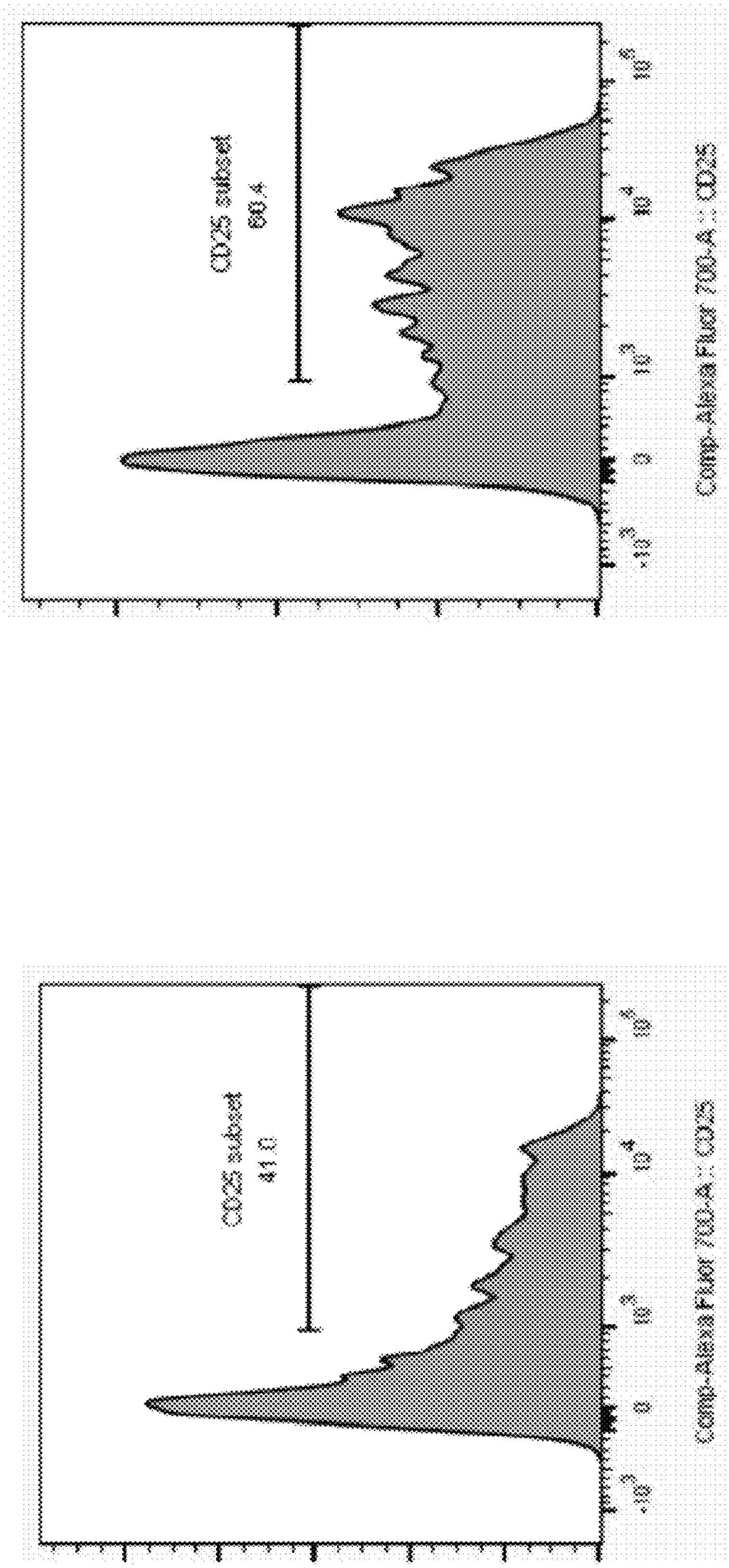
FIG. 20 is a flow cytometry examination diagram showing co-culture of anti-PD-1 scFv erythrocytes and T cells.

As shown in FIGS. 19-20, the anti-PD-1 scFv erythrocytes activated T cells in an in vitro co-culture condition, made T cells proliferated in large numbers, and the detection results of flow cytometry showed that the expression of CD25 was increased.

To sum up, in the method provided in the present invention for preparing the genetically engineered erythrocytes carrying an anti-PD-1 single chain antibody, erythrocytes were used as transport vehicles and were subjected to genetic engineering modification, such that erythrocyte membrane surface carried an antibody medicament (namely, anti-PD-1 single chain antibody) for tumor immunotherapy, afterwards, the genetically engineered precursor cells were induced to differentiate into mature erythrocytes by inducing erythroid differentiation means, thus the genetically engineered erythrocytes carrying the anti-PD-1 single chain antibody were obtained. The genetically engineered erythrocytes carrying an anti-PD-1 single chain antibody provided by the present invention perform targeted delivery of the anti-PD-1 single-chain antibody to tumor tissues, are more effective in exerting T cell activation function, and can significantly reduce the dosage of medicaments and alleviate the side effects of systemic tumor immune medicaments.

The above mentioned are merely preferred feasible embodiments of the present invention, but are not constructed as limiting the present invention. Moreover, the present invention is not limited to the above examples. Any variation, modification, addition or replacement made within the spirit of the present invention by a person skilled in the art shall fall within the protection scope of the present invention.

The invention claimed is:

1. A method for preparing genetically engineered erythrocytes carrying an anti-programmed death-1 single chain variable fragment (anti-PD-1 scFv), characterized by comprising the following steps:

step S1: inserting a desired fragment sequence into a lentiviral expression vector to obtain a vector encoding the desired fragment sequence, wherein the desired fragment sequence is an anti-PD-1 scFv coding sequence;

step S2: packaging the vector encoding the desired fragment sequence from step S1 in a lentiviral particle and obtaining a lentiviral concentrate;

step S3: isolating lineage (Lin) negative and Cluster of Differentiation 34 (CD34) negative cells ($Lin^-CD34^-$ cells) from peripheral blood mononuclear cells, and enriching the $Lin^-CD34^-$ cells by culturing the isolated $Lin^-CD34^-$ cells in a culture medium comprising a cytokine composition for the enrichment of the $Lin^-CD34^-$ cells comprising 50-100 nanogram per milliliter (ng/ml) recombinant human feline McDonough sarcoma (fms)-like tyrosine kinase 3 ligand, 50-100 ng/ml recombinant human stem cell factor, 50-100 ng/ml recombinant human interleukin 3, and 200-800 picogram per milliliter (pg/ml) recombinant human interleukin 6;

step S4: changing the culture medium of the $Lin^-CD34^-$ cells to a differentiation stage-1 culture medium comprising Iscove's modified Dulbecco's medium (IMDM), 10-15% fetal calf serum, 5-10% human plasma, 1-4 millimolar (mM) glutamine, 1-2% bovine serum albumin, 300-600 μg/ml human transferrin, 8-13 μg/ml recombinant human insulin, 2% penicillin-streptomycin, 3-5 ng/ml recombinant human interleukin 3, 4-7 Unit per milliliter (U/ml) recombinant human erythropoietin and 100 ng/ml recombinant human stem cell factor, thereby inducing the $Lin^-CD34^-$ cells to differentiate into erythroid cells;

step S5: adding the lentiviral concentrate prepared in the step S2 to the differentiation stage-1 culture medium comprising the cells obtained in the step S4, wherein the lentiviral concentrate infects the cells obtained in the step S4 to obtain anti-PD-1 scFv carrying cells;

step S6: changing the culture medium of the anti-PD-1 scFv carrying cells to a differentiation stage-2 culture medium comprising IMDM, 15% fetal calf serum, 5-10% human plasma, 1-4 mM glutamine, 1-2% bovine serum albumin, 300-600 μg/ml human transferrin, 8-13 μg/ml recombinant human insulin, 2% penicillin-streptomycin, and 1-5 U/ml recombinant human erythropoietin; wherein the anti-PD-1 scFv carrying cells are subjected to erythrocyte enucleation to obtain mature anti-PD-1 scFv carrying erythrocytes, which are the genetically engineered erythrocytes carrying an anti-PD-1 scFv.

2. The method for preparing the genetically engineered erythrocytes carrying the anti-PD-1 scFv according to claim 1, wherein in the step S1, the anti-PD-1 scFv is encoded by a nucleotide sequence of one of the nucleotide sequences of SEQ ID NO.1, SEQ ID NO.2, SEQ ID NO.3, SEQ ID NO.4, SEQ ID NO.5 or SEQ ID NO.6;

the lentiviral expression vector is the CMV promoter-driven Doxycycline-inducible shRNA & High-titer packaging-Multiple Cloning Site-Thosea asigna virus 2A peptide-codon-optimized Green Fluorescent Protein-promotor of Murine Stem Cell Virus plasmid (pCDH-MCS-T2A-copGFP-MSCV).

3. The method for preparing the genetically engineered erythrocytes carrying the anti-PD-1 scFv according to claim 1, wherein packaging the vector in step S2 comprises incubating human embryonic kidney 293T cells (HEK 293T cells) with a three-plasmid packaging system in culture; wherein the three-plasmid packaging system comprises a vector encoding the desired fragment sequence, a second-generation Packaging System Packaging Plasmid (PSPAX2 plasmid), and a plasmid encoding a Vesicular Stomatitis Virus Glycoprotein (VSVG plasmid); wherein the vector encoding the desired fragment sequence, the PSPAX2 plasmid, and the VSVG plasmid have a ratio of 2:1:1;

and wherein obtaining a lentiviral concentrate comprises centrifuging the HEK293T cell culture following incubation and concentrating a viral suspension at a rotary speed of 70000 relative centrifugal force (RCF), time of 2 hours and a temperature of 4 Celsius degree (° C.).

4. The method for preparing the genetically engineered erythrocytes carrying the anti-PD-1 scFv according to claim 1, wherein the step S3 is performed by resuspending the peripheral blood mononuclear cells in a cell separation buffer solution added with bovine serum albumin and ethylenediaminetetraacetic acid (EDTA); removing cells with surface markers of Lin and CD34 by adding a biotin-labeled antibody and a streptavidin-labeled magnetic bead, thus isolating the $Lin^{-}CD34^{-}$ cells.

5. The method for preparing the genetically engineered erythrocytes carrying the anti-PD-1 scFv according to claim 1, wherein the step S5 is performed by resuspending in the differentiation stage-1 culture medium the cells obtained in the step S4 to obtain a cell suspension;

preparing an infection volume consisting of the cell suspension volume and a volume of the lentiviral concentrate obtained in step S2; and preparing the lentiviral concentrate at a final concentration of $5\times10^{7}$ Transducing Unit per milliliter (TU/ml)-$5\times10^{8}$ TU/ml;

and in terms of the infection volume, adding polybrene to the lentiviral concentrate in the amount of 10 μg/ml for mixed incubation for 5 min, then adding the incubated lentiviral concentrate to the cells and mixing; using a horizontal rotor centrifugal machine for centrifugal infection with a rotary speed of 500 times gravity (×g), a temperature of 32° C. and a time of 90 min; after the centrifugation, placing the anti-PD-1 scFv carrying cells under conditions of 37° C. and 5% carbon dioxide ($CO_2$) for culture.

6. Isolated genetically engineered erythrocytes carrying an anti-PD-1 scFv, wherein the genetically engineered erythrocytes carrying the anti-PD-1 scFv are obtained via the method for preparing the genetically engineered erythrocytes carrying the anti-PD-1 scFv according to claim 1.

* * * * *